US007947040B2

(12) United States Patent
Davies et al.

(10) Patent No.: US 7,947,040 B2
(45) Date of Patent: May 24, 2011

(54) METHOD OF SURGICAL PERFORATION VIA THE DELIVERY OF ENERGY

(75) Inventors: Gareth Davies, Toronto (CA); Amanda April Hartley, Brampton (CA); Naheed Visram, Wimbledon (GB); Krishan Shah, Mississauga (CA); Frank Baylis, Beaconsfield (CA)

(73) Assignee: Baylis Medical Company Inc, Montreal (CA)

( * ) Notice: Subject to any disclaimer, the term of this patent is extended or adjusted under 35 U.S.C. 154(b) by 1559 days.

(21) Appl. No.: 11/265,304

(22) Filed: Nov. 3, 2005

(65) Prior Publication Data
US 2006/0142756 A1   Jun. 29, 2006

Related U.S. Application Data

(63) Continuation-in-part of application No. 10/666,301, filed on Sep. 19, 2003, now Pat. No. 7,048,733, and a continuation-in-part of application No. 10/760,479, filed on Jan. 21, 2004, now Pat. No. 7,270,662, and a continuation-in-part of application No. 10/666,288, filed on Sep. 19, 2003, now abandoned, which is a continuation-in-part of application No. 10/347,366, filed on Jan. 21, 2003, now Pat. No. 7,112,197, application No. 11/265,304.

(60) Provisional application No. 60/522,753, filed on Nov. 3, 2004.

(51) Int. Cl.
*A61B 18/18* (2006.01)
(52) U.S. Cl. ............... 606/45; 606/34; 606/41
(58) Field of Classification Search ............. 606/41–50; 600/433; 604/22, 264
See application file for complete search history.

(56) References Cited

U.S. PATENT DOCUMENTS

| | | | |
|---|---|---|---|
| 3,448,739 | A | 6/1969 | Stark et al. |
| 3,595,239 | A | 7/1971 | Petersen |
| 4,641,649 | A | 2/1987 | Walinsky et al. |
| 4,682,596 | A | 7/1987 | Bales et al. |
| 4,892,104 | A | 1/1990 | Ito et al. |
| 4,928,693 | A | 5/1990 | Goodin et al. |
| 4,936,281 | A | 6/1990 | Stasz |
| 5,098,431 | A | 3/1992 | Rydell |
| 5,281,216 | A | 1/1994 | Klicek |

(Continued)

FOREIGN PATENT DOCUMENTS
EP      0315730      5/1989
(Continued)

OTHER PUBLICATIONS

CA Pedra, LN De Sousa, SR Pedra, WP Ferreira, SL Braga, CA Esteves, MV Santant, JE Sousa, VF Fontes. "New Percutaneous Techniques for Perforating the Pulmonary Valve in Pulmonary Atresia with Intact Ventricular Septum". Arq. Bras Cariol. 77(5):471-478 (2001).

(Continued)

*Primary Examiner* — Roy D Gibson

(57) ABSTRACT

A method of surgical perforation via the delivery of electrical, radiant or thermal energy comprising the steps of: introducing an apparatus comprising an energy delivery device into a patient's heart via the patient's superior vena cava; positioning the energy delivery device at a first location adjacent material to be perforated; and perforating the material by delivering energy via the energy delivery device; wherein the energy is selected from the group consisting of electrical energy, radiant energy and thermal energy.

30 Claims, 21 Drawing Sheets

U.S. PATENT DOCUMENTS

| | | | |
|---|---|---|---|
| 5,364,393 | A | 11/1994 | Auth et al. |
| 5,403,338 | A | 4/1995 | Milo |
| 5,423,809 | A | 6/1995 | Klicek |
| 5,545,200 | A | 8/1996 | West et al. |
| 5,571,088 | A | 11/1996 | Lennox et al. |
| 5,575,772 | A | 11/1996 | Lennox |
| 5,599,347 | A | 2/1997 | Hart et al. |
| 5,673,695 | A | 10/1997 | McGee et al. |
| 5,683,366 | A | 11/1997 | Eggers et al. |
| 5,741,249 | A | 4/1998 | Moss et al. |
| 5,814,028 | A | 9/1998 | Swartz et al. |
| 5,893,848 | A | 4/1999 | Negus et al. |
| 5,893,885 | A | 4/1999 | Webster, Jr. |
| 5,904,679 | A | 5/1999 | Clayman |
| 5,921,957 | A | 7/1999 | Killion et al. |
| 6,009,877 | A * | 1/2000 | Edwards ................... 128/898 |
| 6,093,185 | A | 7/2000 | Ellis et al. |
| 6,106,520 | A | 8/2000 | Laufer |
| 6,146,380 | A | 11/2000 | Racz et al. |
| 6,156,031 | A * | 12/2000 | Aita et al. ................... 606/33 |
| 6,171,305 | B1 | 1/2001 | Sherman |
| 6,293,945 | B1 | 9/2001 | Parins et al. |
| 6,296,615 | B1 | 10/2001 | Brockway et al. |
| 6,360,128 | B2 | 3/2002 | Kordis et al. |
| 6,565,562 | B1 | 5/2003 | Shah et al. |
| 6,632,222 | B1 | 10/2003 | Edwards et al. |
| 6,650,923 | B1 | 11/2003 | Lesh et al. |
| 6,702,811 | B2 | 3/2004 | Stewart et al. |
| 6,811,544 | B2 | 11/2004 | Schaer |
| 6,814,733 | B2 | 11/2004 | Schwartz |
| 6,869,431 | B2 | 3/2005 | Maguire et al. |
| 2002/0087156 | A1 | 7/2002 | Maguire et al. |
| 2002/0123749 | A1 | 9/2002 | Jain |
| 2002/0169377 | A1 | 11/2002 | Khairkhahan et al. |
| 2004/0133113 | A1 | 7/2004 | Krishnan |
| 2006/0074398 | A1 | 4/2006 | Whiting |
| 2006/0079769 | A1 | 4/2006 | Whiting |
| 2006/0079787 | A1 | 4/2006 | Whiting |

FOREIGN PATENT DOCUMENTS

| | | |
|---|---|---|
| EP | 1169976 A1 | 1/2002 |
| WO | WO-93/20747 | 10/1993 |
| WO | WO-02/058780 A1 | 8/2002 |
| WO | WO-2004/026134 A1 | 4/2004 |
| WO | WO-2004/039433 | 5/2004 |

OTHER PUBLICATIONS

DG Nykanen, J Phikala, GP Taylor, LN Benson. "Radiofrequency Assisted Perforation of the Atrial septum in a Swine Model: Feasibility, Biophysical and Histological Characteristics". Circulation. 100(Suppl 1):1-804 (1999).

Baylis Medical Company Inc. "Radio Frequency Perforation System". 2001.

"Abstract of European Patent No. 0315730 to Osypka". (1989).

Benson, Lee N., David Nykanen, Amanda Collison. "Radiofrequency Perforation in the Treatment of Congenital Heart Disease". Catheterizations and Cardiovascular Interventions. 56: 72-82 (2002).

Conti C.R. "Transseptal Left Heart Catheterization for Radiofrequency Ablation of Accessory Pathways". Clinical Cardiology. 16: 367-368 (1993).

Justino, Henri, Lee N. Benson, David G. Nykanen. "Transcatheter Creation of an Atrial Septal Defect Using Radiofrequency Perforation". Catheterization and Cardiovascular Interventions. 56: 412-415 (2002).

Kamal K. Sethi, Jagdish C. Mohan. "Editorial Comment: Transseptal Catheterization for the Electrophysiologist: Modification with a 'View'". Journal of Interventional Cardian Physiology. 5: 97-99 (2001).

Christodoulos Stefanadis. "Retrograde Nontransseptal Balloon Mitral Valvuloplasty: Immediate Results and Intermediate Long-term Outcome in 441 Cases—A Multicentre Experience". Journal of the American College of Cardiology. 32(4):1009-16 (1998).

N. Shimko, P. Savard, K. Shah. "Radiofrequency Perforation of Cardiac Tissue: Modeling and Experimental Results". Med. Biol. Eng. comput. 38:575-582 (2000).

Boston Scientific Corporation. "http://www.bostonscientific.com/med_specialty/deviceDetail.sp?task=tskBasicDevice.jsp&sectionid=4&relld=1, 20,21,22&deviceid=1888&uniqueid=MP0858". Explorer ST Catheters. 2 pages. (Date of Printing—Jun. 2005).

Boston Scientific Corporation. "http://www.bostonscientific.com/med_specialty/deviceDetail.sp?task=tskBasicDevice.jsp&sectionid=4&relld=2, 74,75,76&deviceid=11026&uniqueid=MPDB2799". PT2 Guidewires. 2 pages. (Date of Printing—Jun. 2005).

IntraLuminal Therapeutics, Inc. "http://www.intraluminal.com/products/catheter.html". Safe Cross Support Catheter. 1 page. (Date of Printing—Jun. 2005).

Lake Region Manufacturing, Inc. "http://www.lakergn.com/jmc.htm". Paragon Guidewire. 2 pages (Date of Printing—Jun. 2005).

Medtronic Inc. "http://www.medtronic.com/epsystems/diagnostic_catheters.html". Diagnostic Catheters. 7 pages (Date of Printing—Apr. 2005).

Johnson & Johnson Gateway, LLC. "http://www.jnjgateway.com/home.html?loc=USENG&page=viewcontent&contentid=ic0de00100001135&nodekey=/prod_info/Specialty/arrhyth mia_management/electrophysiology/EP_diagnostic_catheters". EP Diagnostic Catheters. 2 pages. (Date of printing—Jun. 2005).

Johnson & Jonhson Gateway, LLC. "http//www.jnjgateway.com/home.html.sessionid=JNSFHTWOAOIC0CQPCCECPJYKB2WNSC?loc=USENGA&page=viewcontent & contentid=ic0de00100000524&nodekey=/prod_info/specialty/cardiovascular_and_thoracic/cardiac_diagnosis_interventions/diagnostic_wires&_request=228905". Diagnostic Guidewires. 4 pages (Date of Printing—Jun. 2005).

T Abdel-Massih, Y Boudjemline, p. Bonhoeffer. "Unusual Interventional Management in an Adult with Tetraogy of Fallot". Cardiol Young. 13(2):2003-2005. Apr. 2003.

T Humpl, B Soderberg, BW McCrindle, DG Nykanen, RM Freedom, WG Williams, LN Benson. "Percutaneous Balloon Valvotomy in Pulmonary Atresia with Intact Ventricular Septum: Impact on Patient Care". Circulation. 108(7): 826-832 (Aug. 2003).

CA Pedra, RM Filho, RS Arrieta, R Tellez, VF Fontes. "Recanalizationof a discrete atretic right pulmonary artery segment with a new radiofrequency system". Catheter Cardiovasc. Interv. 60(1):82-87 (Sep. 2003).

HW Kort, DT Balzer. "Radiofrequency perforation in the treatment of acquired left pulmonary atresia following repair of tetralogy of fallot". Catheter Cardiovasc. Interv. 60(1): 79-81 (Sep. 2003).

G. Veldtman, A Peirone, LN Benson. "Radiofrequency perforation of the atrial system: Preliminary experimental evaluation and development." PICS VII Abstracts. Catheter Cardiovasc. Interv. 60(1):132 (Sep. 2003).

F. Godart, C. Francart, GM Breviere, C Rey. "Pulmonary valvulotomy with the Nykanen Radiofrequency guide in pulmonary atresia with intact interventricular septum". Arch Mal Couer Vaiss. 86(5):517-520 (May 2003). Article is in French with English Summary.

T. Szili-Torok, G.P. Kimman, D. Theuns, J. Res, J.R.T.C. Roelandt, L.J. Jordaens. "Transseptal Left heart Catheterization Guided by Intracardiac Echocardiography". Heart 2001; 86: e11.

Hector Biddogia, Juan P. Maciel, Jose A. Alvarez et al. "Transseptal Left Heart Catheterization: Usefulness of the Intracavitary Electrocardiogram in the Localization of the Fossa Ovalis". Catheterization and Cardiovascular Diagnosis 24: 221-225 (1991).

George Joseph, G. Rajendiran, K. Abhaichand Rajpal. "Transjugular Approach to Concurrent Mitral-Aortic and Mitral-Tricuspid Balloon Valvuloplasty". Catheterization and Cardiovascular Interventions 49:335-341 (2000).

George Joseph, Oommen K. George, Asishkumar Mandalay, Sunil Sathe. "Transjugular Approach to Balloon Mitral Valvuloplasty Helps Overcome Impediments Caused by Anatomical Alterations". Catheterization and Cardiovascular Interventions 57:353-362 (2002).

George Joseph, Dibya K. Baruah, Sajy V. Kuruttukumlam, Sunil Thomas Chandy, Shanker Krishnaswami. "Transjugular Approach toTransseptal Balloon Mitral Valvuloplasty". Catheterization and Cardiovascular Diagnosis 42:219-226 (1997).

Tsung O. Cheng. "All Roads Lead to Rome:Transjugular or Transfemoral Approach to Percutaneous Transseptal Balloon Mitral Valvuloplasty?". Catheterization and Cardiovascular Interventions 59:266-267 (2003).

J. Thompson Sullebarger, Humberto Coto, Enrique Lopez, Dany Sayad, Hector L. Fontanet. "Transjugular Percutaneous Inoue Balloon Mitral Commissurotomy in a Patient With Inferior Vena Cava Obstruction After Liver Transplantation". Catheterization and Cardiovascular Interventions 59:261-265 (2003).

Georgejoseph, K.P. Suresh Kumar, Paul V. George, Subodh Dhanawade. "Right Internal Jugular Vein Approach as an Alternative in Balloon Pulmonary Valvuloplasty". Catheterization and Cardiovascular Interventions 46:425-429 (1999).

Pressure Products, Inc. http://www.pressure-products.com/Downloads/Education_PDFs/Using_CSG_v2.pdf. 4 pages. 2005.

Gideon J. DU Marchie Sarvaas, MD, Kalyani R. Trivedi, MD, Lisa K. Hornberger, MD, K. Jin Lee, MD, Joel A. Kirsh, MD, and Lee N. Benson, MD. "Radiofrequency-Assisted Atrial Septoplasty for an Intact Atrial Septum in Complex Congenital Heart Disease". Catheterization and Cardiovascular Interventions 56:412-415 (2002).

\* cited by examiner

METHOD OF SURGICAL PERFORATION VIA THE DELIVERY OF ENERGY

CROSS-REFERENCES TO RELATED APPLICATIONS

This application is a continuation-in-part of co-pending U.S. application Ser. No. 10/666,301, filed Sep. 19, 2003 and a continuation-in-part of co-pending U.S. application Ser. No. 10/760,479, filed Jan. 21, 2004 and a continuation-in-part of co-pending U.S. application Ser. No. 10/666,288, filed Sep. 19, 2003, which is a continuation-in-part of co-pending U.S. application Ser. No. 10/347,366, filed Jan. 21, 2003. This application also claims the benefit of U.S. provisional application Ser. No. 60/522,753, filed Nov. 3, 2004.

TECHNICAL FIELD

The invention relates to a method, and device therefore, for creating a perforation in a patient material via energy delivery.

BACKGROUND OF THE ART

Trans-septal catherization procedures typically involve insertion of a needle, such as the trans-septal needle of Cook Incorporated (Bloomington, Ind., USA) into a patient's heart. The needle comprises a stiff metal cannula with a sharpened distal tip. The needle is generally introduced through a dilator and guiding sheath set in the femoral vein and advanced through the vasculature into the right atrium. From there the needle tip is positioned at the fossa ovalis, the preferred location on the septum for creating a puncture. Using a needle trans-septal puncture is complicated by the necessity of accessing the heart through the femoral vein and inferior vena cava. Occasionally, due to abnormalities of the venous system such as azygous continuation of the inferior vena cava or thrombosis or obliteration of the iliofemoral veins it may not be possible to gain access to the right atrium using a femoral approach. In addition, the standard femoral transvenous approach to the atrial septum for trans-septal access, as described earlier, may be difficult in situation where the cardiac anatomy is grossly distorted such as in patients with longstanding and marked elevation of left atrial and pulmonary artery pressures, or patients who have previously undergone cardiac surgery. Gaining trans-septal access from the femoral approach may also be difficult in patients with dextrocardia, a condition in which the heart is located on the right side of the chest rather than the left and in whom there is significant variation in the orientation of the atrial septum.

A trans-jugular approach, using a needle to gain trans-septal access, is described by Joseph et. al. (1997). Joseph states that trans-jugular septal puncture may find application in cardiac electrophysiology because it offers a more direct approach to the mitral annulus, left ventricle, and inferior aspect of the left atrium. In another publication by Joseph et. al. (2000), the author states that in transvenous mitral valvuloplasty, the jugular approach simplifies septal puncture and mitral valve crossing in patients with a huge left atrium and distorted anatomy, besides making the procedure feasible in the presence of obstruction of the inferior vena cava. However, needle trans-septal punctures from the jugular approach are more difficult to perform and require significant practice. Cheng (2003), commenting on the aforementioned articles, states that the transjugular approach for trans-septal needle puncture is more difficult to perform than the transfemoral approach and that only with larger studies and more experience will we be able to tell whether the innovative tranjugular approach is as versatile, efficacious, and safe as the conventional transfemoral approach.

U.S. Pat. No. 6,565,562 to Shah et al., entitled "Method for the radio frequency perforation and the enlargement of a body tissue" issued May 20, 2003, describes a method of perforating tissue using a radiofrequency (RF) perforating device. A functional tip on the RF perforating device is placed against target tissue and as RF current is applied a perforation is created. This method allows the RF perforating device to easily pass through the tissue without applying significant force that could cause the tissue to tent. However, Shah et al. do not describe employing such a device using a non-femoral approach to perforate bodily tissue, which would require a means of positioning the perforation device appropriately to allow for perforation and/or dilation.

The SafeSheath® CSG Worley, described in the publication entitled "Using the Pressure Products SafeSheath CSG Worley with Radio Opaque Soft-Tipped Braided Core" is a surgical sheath designed to be introduced into a patient's heart through the Superior Vena Cava (SVC) and on through the coronary sinus. The SafeSheath® device is not intended or structured to allow for perforation of patient material nor is it structured to allow for positioning within a patient's heart for perforation and/or dilation.

Thus, patients requiring trans-septal punctures would benefit from a device that utilizes a non-femoral, i.e. superior, approach and which is more reliable and user-friendly than the trans-septal needle. In particular, the patient population discussed above would benefit from a device and technique for trans-septal perforation that allows for a multiplicity of uncomplicated intravascular approaches as well as providing a more controlled method of perforation.

SUMMARY OF THE INVENTION

A broad object of the present invention is to overcome the disadvantages and limitations of the prior art in a novel and non-obvious manner by providing a method for creating a surgical perforation via the delivery of electrical, thermal or radiant energy. This is accomplished by describing a method, and device therefore, for introducing an apparatus into a patient's heart, positioning at least a portion of the apparatus at an appropriate location and delivering energy to create a perforation at the location. Advantageously, the apparatus may be introduced via the superior vena cava, which may be useful in instances where a femoral approach is contra-indicated. The apparatus may include an energy delivery device which may be operable to deliver energy such as electrical, radiant or thermal energy. The method may further comprise a step of advancing the energy delivery device through the perforation and optionally dilating the perforation to allow, for example, for the insertion of further devices and/or treatment compositions across the perforation.

BRIEF DESCRIPTION OF THE DRAWINGS

In order that the invention may be readily understood, embodiments of the invention are illustrated by way of examples in the accompanying drawings, in which.

It will be noted that throughout the appended drawings, like features are identified by like reference numerals.

DETAILED DESCRIPTION OF THE INVENTION

Definition

RF Ablation vs. RF Perforation

Figure 1:
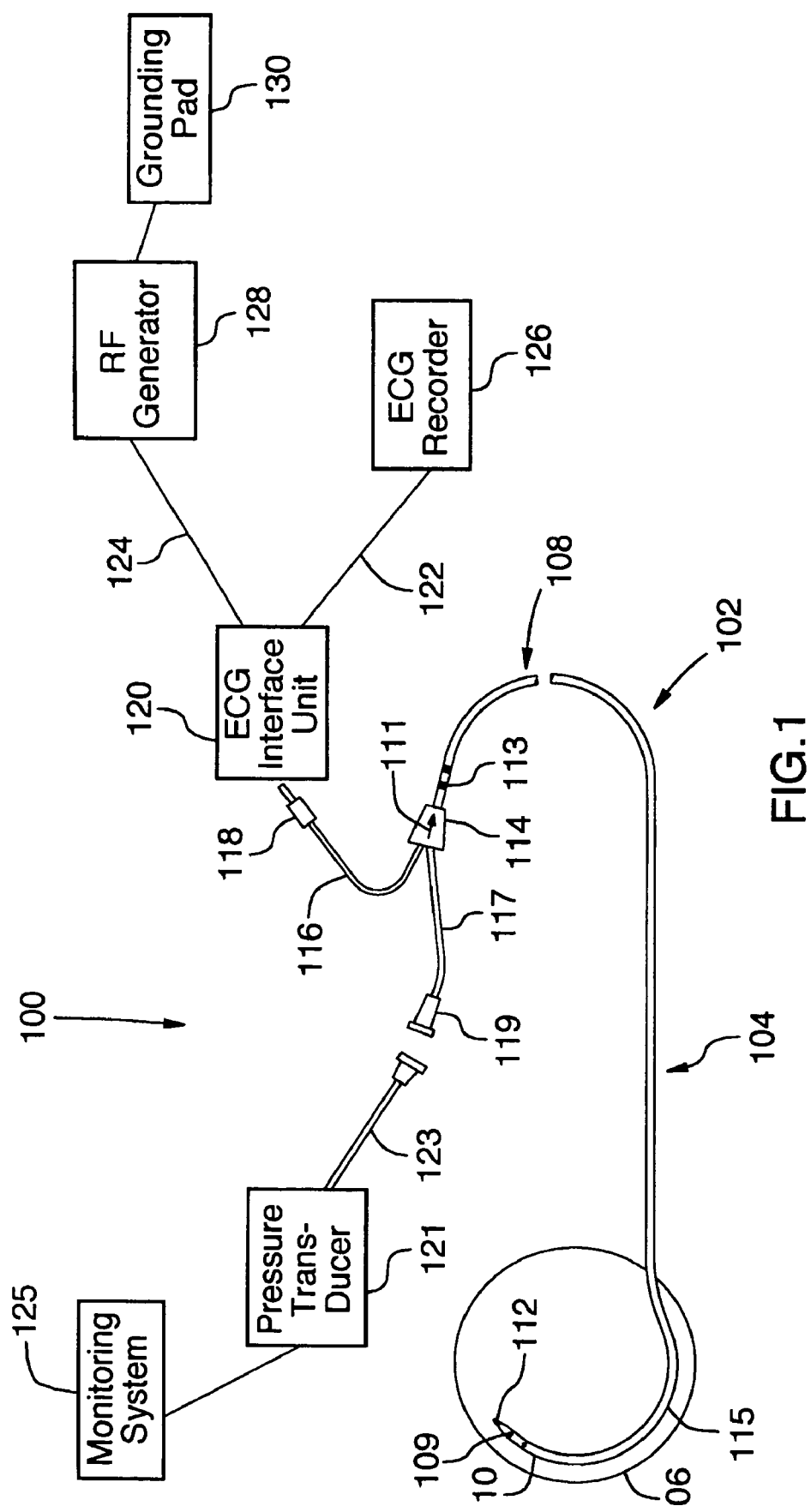
FIG. 1 illustrates a schematic view of an electrosurgical system including an electrosurgical device in accordance with an embodiment of the invention.

Benson et. al. (2002) discuss the fundamental differences between RF ablation and RF perforation. In an RF perforation procedure, energy is applied to rapidly increase tissue temperature to the extent that the intracellular fluid becomes converted to steam, inducing cell lysis as a result of elevated pressure within the cell. Upon the occurrence of cell lysis and rupture, a void is created, allowing the tip of the catheter to penetrate the tissue. In order to achieve this effect, RF perforation devices must apply a high voltage to the tissue region over a short period of time. Also, the tip of the device being used should be relatively small, in order to increase the impedance of the device. This is in contrast to RF ablation, whereby a larger-tipped device is utilized to deliver a low impedance and high power signal to the region involved. Furthermore, as opposed to RF perforation, which creates a void in the tissue through which the device may be advanced, the objective of RF ablation is to create a large, non-penetrating lesion in the tissue, in order to disrupt electrical conduction. Thus, for the purposes of the present invention, perforation is defined as the creation of a void within a material.

With specific reference now to the drawings in detail, it is stressed that the particulars shown are by way of example and for purposes of illustrative discussion of embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Electrosurgical Device

FIG. 1 illustrates an embodiment of an apparatus 102 in a system 100. Apparatus 102 comprises an elongate member 104 having a distal region 106, and a proximal region 108. Distal region 106 is adapted to be inserted within and along a lumen of a body of a patient, such as a patient's vasculature, and maneuverable therethrough to a desired location proximate material, such as tissue, to be perforated.

Figure 2:
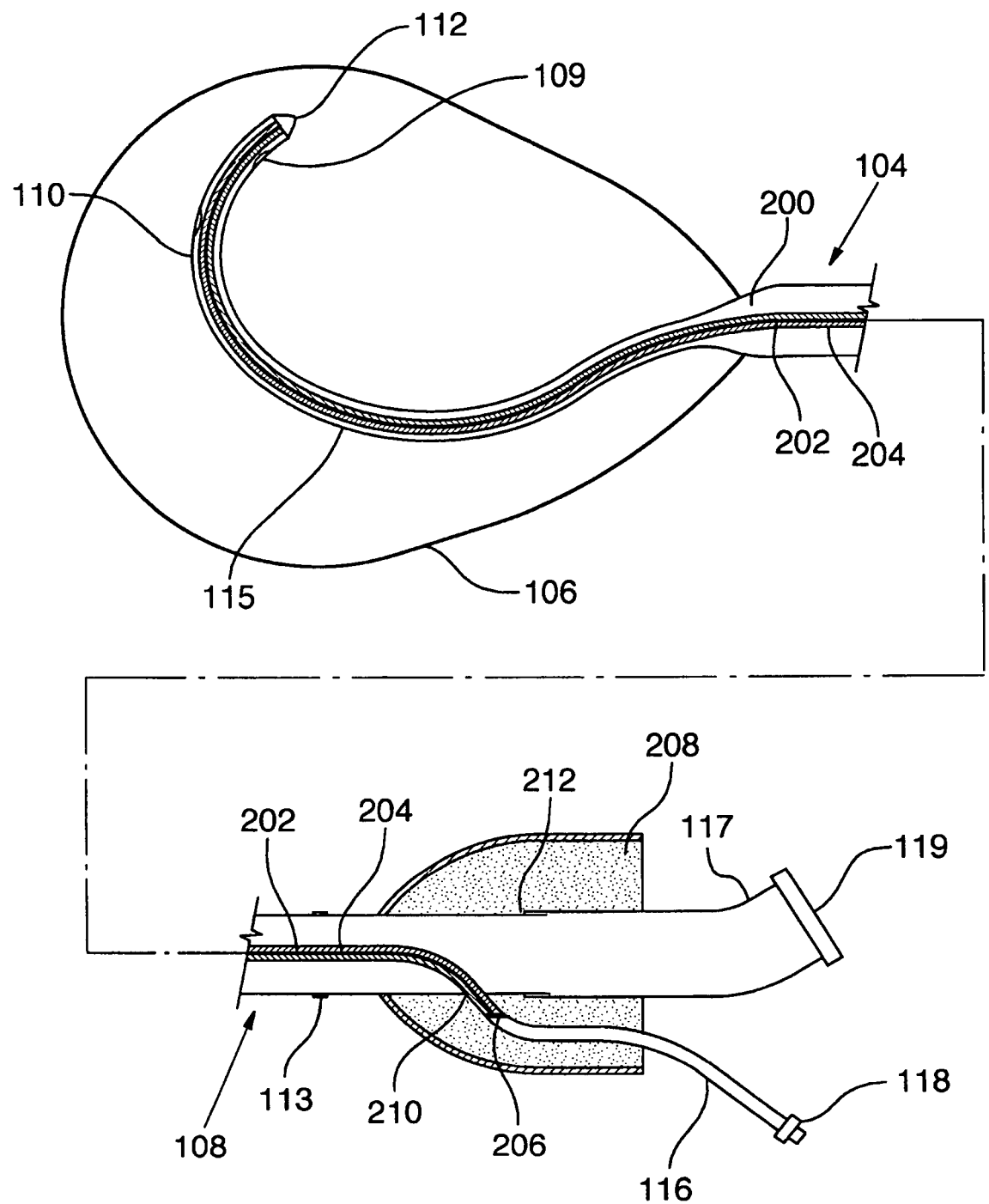
FIG. 2 illustrates a side cross-sectional view of the device of FIG. 1.

In some embodiments, the elongate member 104 may be tubular in configuration, having at least one lumen extending from proximal region 108 to distal region 106 such as lumen 200 shown in FIG. 2. Elongate member 104 may be constructed of a biocompatible polymer material that provides column strength to apparatus 102. The elongate member 104 is sufficiently stiff to permit a dilator 910 and a guiding sheath 800 (See FIG. 8) to be easily advanced over apparatus 102 and through a perforation. Examples of suitable materials for the tubular portion of elongate member 104 are polyetheretherketone (PEEK), and polyimide. In the illustrated embodiment, the outer diameter along the tubular portion of elongate member 104 tapers down to distal region 106. In alternate embodiments, the outer diameter along elongate member 104 remains substantially constant from proximal region 108 to distal region 106.

Figure 12:
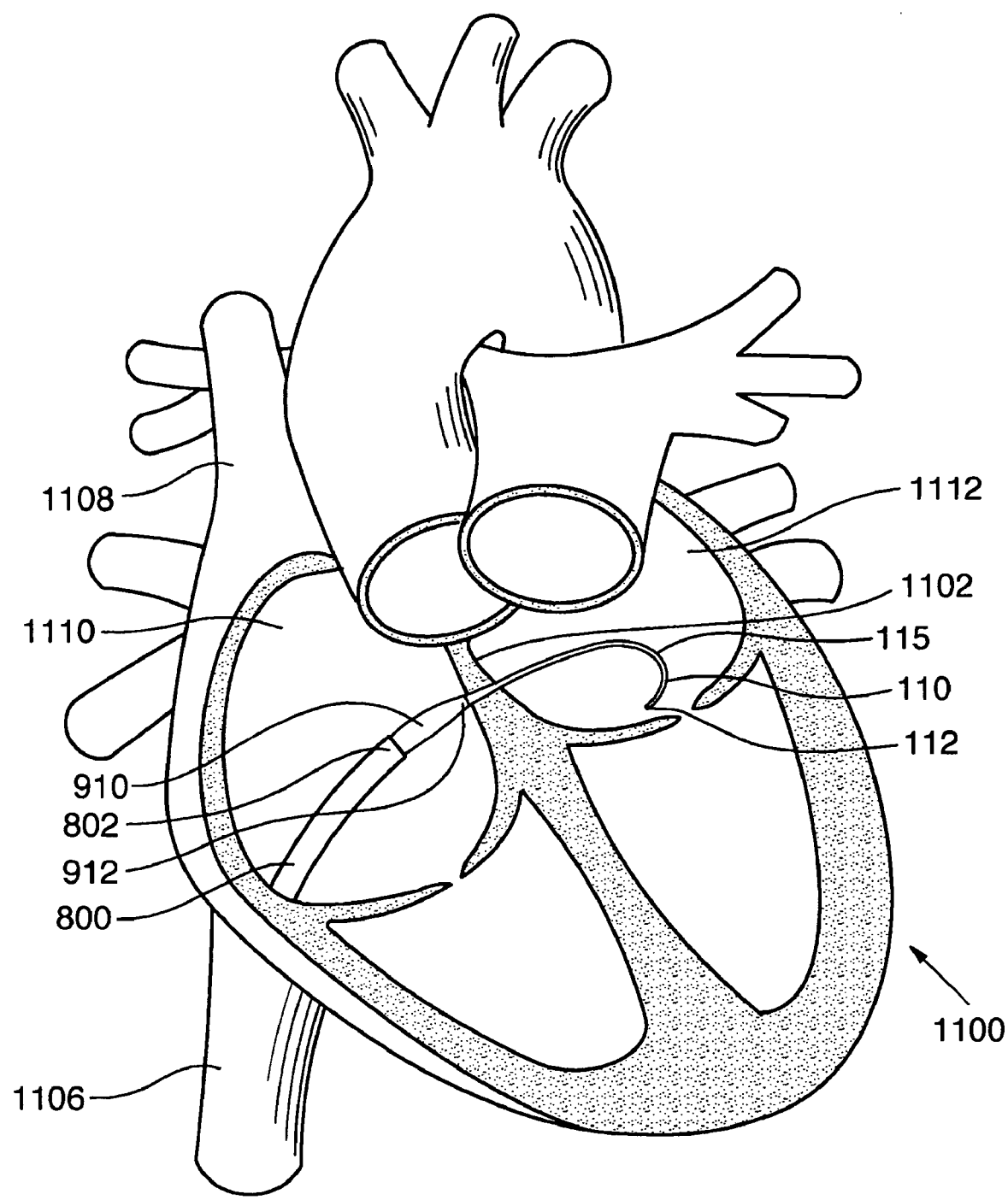
FIG. 12 illustrates a second position of one embodiment of the present invention within a patient's heart.

Distal region 106 is constructed of a softer polymer material so that it is pliable and atraumatic when advanced through vasculature. In some embodiments, the material is also formable, so that its shape can be changed during manufacturing, typically by exposing it to heat while it is fixed in a desired shape. In an alternate embodiment, the shape of distal region is modifiable by the operator during use. An example of a suitable plastic is Pebax (a registered trademark of Atofina Chemicals, Inc.). In the present embodiment, the distal region 106 comprises a curve portion 115. Referring to FIG. 12, as the distal region 106 is advanced out of a guiding sheath, it curls away from the general axis of the sheath which helps ensure that energy delivery device 112 is not in a position to inadvertently injure unwanted areas within a patient's heart after trans-septal perforation. Curve length may be about 4 cm (about 1.57") to about 6 cm (about 2.36") and the curve may traverse about 225 to about 315 degrees of the circumference of a circle. For example, the curve may be about 5 cm in length and may traverse about 270 degrees of the circumference of a circle. Such an embodiment may be useful to avoid unwanted damage to cardiac structures.

In some embodiments, curve portion 115 begins about 0.5 cm to about 1.5 cm proximal to energy delivery device 112, leaving an approximately 1 cm (about 0.39") straight portion in the distal region 106 of apparatus 102. This ensures that this initial portion of apparatus 102 will exit dilator 910 (see FIG. 9 below) without curving, enabling the operator to easily position the apparatus 102, for example, against a septum as described further below. This feature further ensures that the distal region 106 of apparatus 102 will not begin curving within the atrial septum.

Distal region 106 may have a smaller outer diameter compared to the remainder of elongate member 104 so that dilation of a perforation is limited while the distal region 106 is advanced through the perforation. Limiting dilation ensures that the perforation will not cause hemodynamic instability once apparatus 102 is removed. In some embodiments, the outer diameter of distal region 106 may be no larger than about 0.8 mm to about 1.0 mm. For example, the outer diameter of distal region 106 may be about 0.9 mm (about 0.035"). This is comparable to the distal outer diameter of the trans-septal needle that is traditionally used for creating a perforation in the atrial septum. Similarly, in some embodiments, the outer diameter of elongate member 104 may be no larger than about 0.040" to about 0.060". For example, the outer diameter of elongate member 104 may be about 0.050" (1.282 mm), which is also comparable to the trans-septal needle dimensions.

Distal region 106 terminates at functional tip region 110, which comprises a device that functions as an energy delivery device as well as an ECG measuring device. Functional tip region 110 comprises at least one energy delivery device 112 made of a conductive and radiopaque material, such as stainless steel, tungsten, platinum, or another metal. One or more radiopaque markings (not shown) may be affixed to elongate member 104 to highlight the location of the transition from distal region 106 to the remainder of elongate member 104, or other important landmarks on apparatus 102. Alternately, the entire distal region 106 of apparatus 102 may be radiopaque. This can be achieved by filling the polymer material, for example Pebax, used to construct distal region 106 with a radiopaque filler. An example of suitable radiopaque filler is Bismuth. Distal region 106 may contain at least one opening 109 which is in fluid communication with main lumen 200 (FIG. 2) as described further below.

In the illustrated embodiment, proximal region 108 comprises a hub 114, to which are attached a catheter connector cable 116, and connector 118. Tubing 117 and adapter 119 are attached to hub 114 as well. Proximal region 108 may also have one or more depth markings 113 to indicate distances from functional tip region 110, or other important landmarks on apparatus 102. Hub 114 comprises a curve direction or orientation indicator 111 that is located on the same side of apparatus 102 as the curve 115 in order to indicate the direction of curve 115. Orientation indicator 111 may comprise inks, etching, or other materials that enhance visualization or tactile sensation. One or more curve direction indicators may be used and they may be of any suitable shape and size and a location thereof may be varied about the proximal region 108.

In the illustrated embodiment, adapter 119 is configured to releaseably couple apparatus 102 to an external pressure transducer 121 via external tubing 123. External pressure transducer 121 is coupled to a monitoring system 125 that converts a pressure signal from external pressure transducer 121 and displays pressure as a function of time. Catheter connector cable 116 connects to Electro-cardiogram (ECG) interface unit 120 via connector 118. ECG connector cable 122 connects ECG interface unit 120 to ECG recorder 126, which displays and captures ECG signals as a function of time. Generator connector cable 124 connects ECG interface unit 120 to an energy source such as generator 128. In this embodiment, ECG interface unit 120 functions as a splitter, permitting connection of electrosurgical apparatus 102 to both ECG recorder 126 and generator 128 simultaneously. ECG signals can be continuously monitored and recorded and the filtering circuit within ECG interface unit 120 may permit energy, for example RF energy, to be delivered from generator 128 through electrosurgical apparatus 102 without compromising ECG recorder 126.

In another embodiment (not shown) of apparatus 102, there may be a control mechanism associated with the distal region 106 of apparatus 102 and an operating mechanism to operate said control mechanism associated with the proximal region 108 of apparatus 102. The control mechanism may be used to steer or otherwise actuate at least a portion of distal region 106.

Generator 128 may be a radiofrequency (RF) electrical generator that is designed to work in a high impedance range. Because of the small size of energy delivery device 112 the impedance encountered during RF energy application is very high. General electrosurgical generators are typically not designed to deliver energy in these impedance ranges, so only certain RF generators can be used with this device. In one embodiment, the energy is delivered as a continuous wave at a frequency between about 400 kHz and about 550 kHz, a voltage of between 100 to 200 V RMS and a duration of up to 99 seconds. An appropriate generator for this application is the BMC RF Perforation Generator (model number RFP-100, Baylis Medical Company, Montreal, Canada). This generator delivers continuous RF energy at about 460 kHz. A grounding pad 130 is coupled to generator 128 for attaching to a patient to provide a return path for the RF energy when generator 128 is operated in a monopolar mode. Other embodiments could use pulsed or non-continuous RF energy. In still other embodiments of apparatus 102, different energy sources may be used, such as radiant (e.g. laser), ultrasound, thermal or other frequencies of electrical energy (e.g. microwave), with appropriate energy sources, coupling devices and delivery devices.

Referring to FIG. 2 a cross-section of apparatus 102 is illustrated in accordance with the embodiment of FIG. 1. Functional tip region 110 comprises an energy delivery device 112 that is coupled to an insulated conducting wire 202. Conducting wire 202 may be attached to distal region 106 using an adhesive. Alternately, distal region 106 may be melted onto insulation 204 on conducting wire 202 to form a bond.

Conducting wire 202 carries electrical energy from generator 128 to the energy delivery device 112. Conducting wire 202 also carries action potentials or voltage measured by energy delivery device 112 to ECG recorder 126. Action potentials or voltage measured by energy delivery device 112 is with reference to a zero potential or ground electrode (not shown) within ECG recorder 126 or with reference to a ground electrode (not shown) attached to the patient (not shown). Conducting wire 202 is covered with electrical insulation 204 made of a biocompatible material that is able to withstand high temperatures such as polytetrafluoroethylene (PTFE), or other insulating material. Conducting wire 202 may extend through a main lumen 200 of apparatus 102, which lumen may extend from proximal region 108 to distal region 106.

Figure 3:
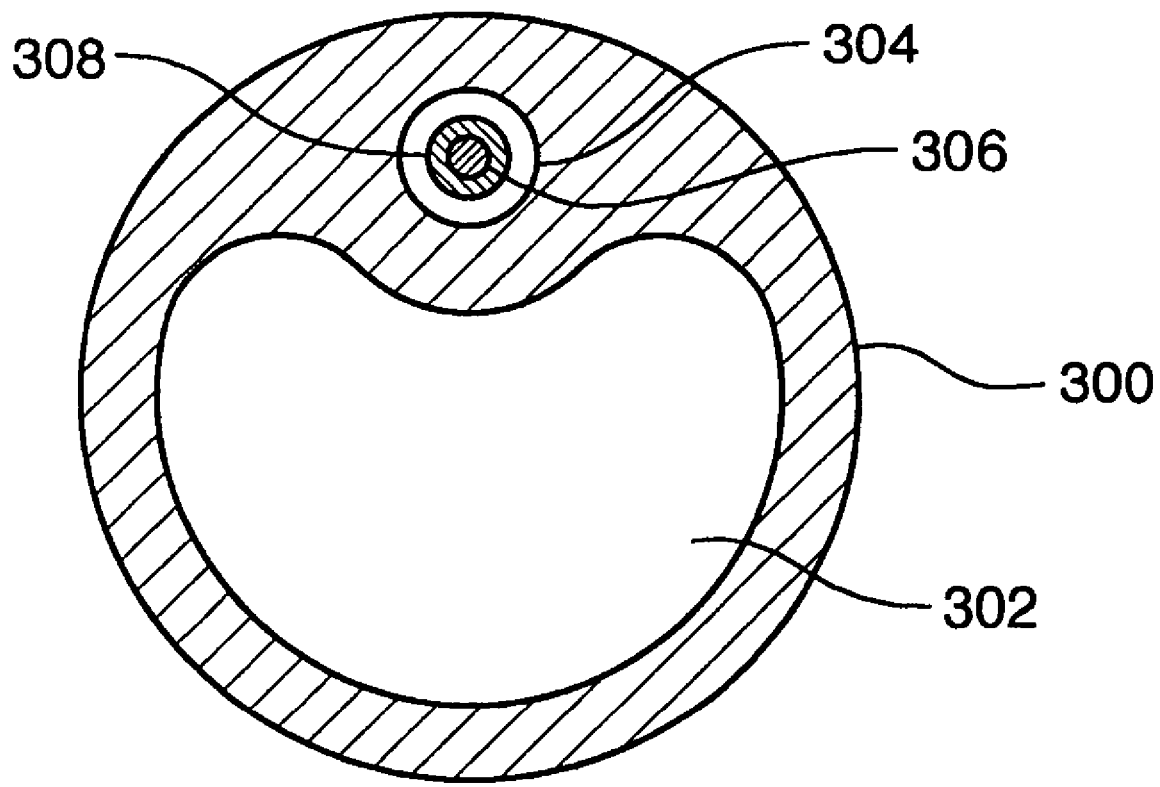
FIG. 3 illustrates a cross-sectional view of an alternate embodiment of the device.

In an alternate embodiment shown in cross section view in FIG. 3, an elongate member 300 comprises main lumen 302 and a separate lumen 304. The separate lumen 304 contains a conducting wire 306 covered with electrical insulation 308 and main lumen 302 can be used for aspiration of blood and injection of contrast (e.g. for staining) and other media. This embodiment of elongate member 300 allows a dedicated lumen for each function of apparatus 102. In yet further embodiments, apparatus 102 may not comprise a lumen and the present invention is not limited in this regard.

In the embodiment of FIG. 2, main lumen 200 extends from proximal region 108 along elongate member 104 and through distal region 106 of apparatus 102. At least one opening 109 at the distal region 106 provides a pathway between main lumen 200 and the environment surrounding distal region 106, such as a desired location within a patient's body. Openings 109 may be sufficiently dimensioned to easily aspirate blood to and through main lumen 200 and to inject radiopaque contrast; however, openings 109 may be limited in number and dimension so that they do not compromise the structural integrity of distal region 106. In order to facilitate even distribution of contrast agent and to prevent pooling in main lumen 200 at distal region 106, openings 109 may be dimensioned such that distally located openings are larger than proximally located openings. The location of openings 109 is as close to energy delivery device 112 as possible so that only a small portion of apparatus 102 is required to extend from dilator 910 and sheath 800 in order to measure pressure. In this embodiment, adapter 119 is configured for releasably coupling to an external pressure transducer 121 or to a standard syringe. For example, adapter 119 comprises a female Luer lock connection. Adapter 119 is coupled to main lumen 200 via tubing 117 to provide a pathway from main lumen 200 to external pressure transducer 121 so that blood pressure can be measured. In embodiments that don't comprise a lumen, apparatus 102 may or may not comprise openings 109.

In the illustrated embodiment, insulated conducting wire 202 exits elongate member 104 through an exit point 210. Exit point 210 may be sealed with an adhesive or a polymeric material. Conducting wire 202 extends along elongate member 104 from distal region 106 to proximal region 108 and is electrically coupled to catheter connector cable 116 within hub 114 by an electrical joint 206. Soldering or another wire joining method can be used to make joint 206. Catheter connector cable 116 terminates with a connector 118 that can mate with either the ECG interface unit 120, or a separate extension connector cable (not shown). Catheter connector cable 116 and connector 118 may be made of materials suitable for sterilization, and may insulate the user from energy traveling through the conductor.

In the illustrated embodiment, elongate member 104 is coupled to tubing 117 at proximal end 212 of elongate member 104. Tubing 117 may be made of a polymeric material that is more flexible than elongate member 104. A suitable material for tubing 117 is polyvinylchloride (PVC), or another flexible polymer. Tubing 117 is coupled to adapter 119. This configuration provides a flexible region for the user to handle when releaseably coupling external pressure transducer 121, or other devices to adapter 119. Couplings between elongate member 104 and tubing 117, and between tubing 117 and adapter 119 may be made with an adhesive such as a UV curable adhesive, an epoxy, or another type of bonding agent.

A hub 114 surrounds electrical joint 206 and proximal end 212 of elongate member 104 in order to conceal the aforementioned connections. The hub 114 may be made of a polymeric material, and may be filled with a filling agent 208 such as an epoxy, or another polymeric material, in order to hold catheter connector cable 116 and tubing 117 in place.

Figure 4:
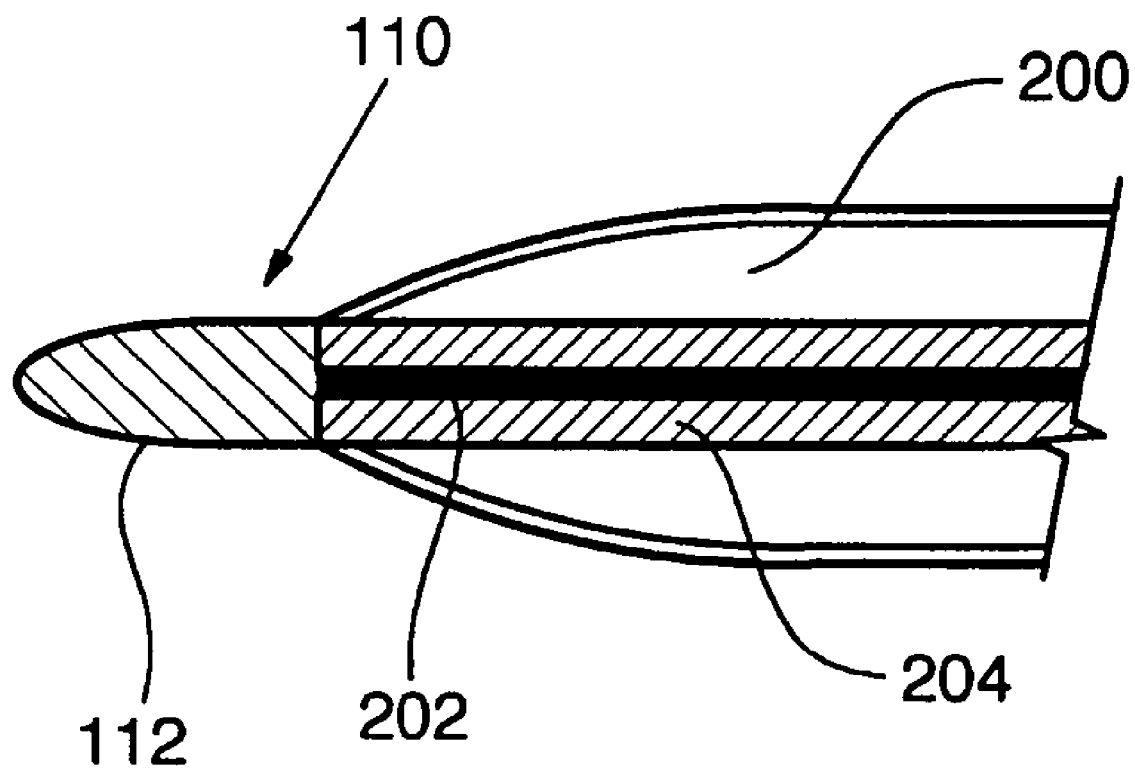
FIG. 4 illustrates an active electrode of the device of FIG. 1.

Referring now to FIG. 4, there is illustrated a side cross-sectional view of an embodiment of functional tip region 110. In one embodiment, functional tip region 110 comprises one energy delivery device 112 configured as an active electrode in a bullet shape. Energy delivery device 112 may be about 0.10 cm to about 0.20 cm in length and may have an outer diameter of about 0.02 cm to about 0.06 cm. For example, energy delivery device 112 may have a length of about 0.15 cm (about 0.059") and may have an outer diameter of about 0.04 cm (about 0.016"). Energy delivery device 112 is coupled to an end of conducting wire 202, which may also be made out of a conductive and radiopaque material. Energy may be delivered through energy delivery device 112 to tissue, and may travel through the patient to grounding pad 130, which is connected to generator 128. Additionally, action potentials or voltage measured from tissue through energy delivery device 112 travel through conducting wire 202 to ECG recorder 126. Alternate embodiments of energy delivery device 112 may be configured in shapes other than a bullet. These shapes include a spherical shape, a rounded shape, a ring shape, a semi-annular shape, an ellipsoid shape, an arrowhead shape, a spring shape and a cylindrical shape, among others.

Figure 5:
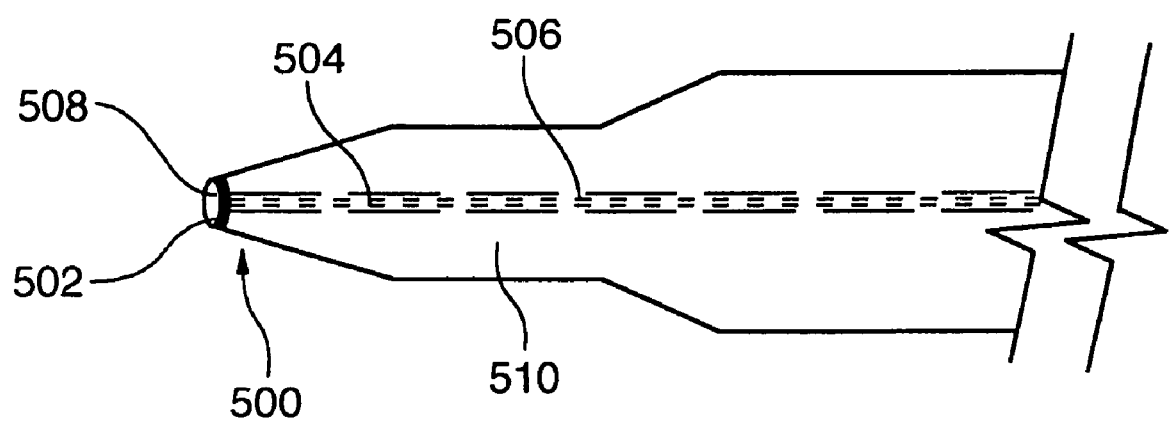
FIG. 5 illustrates the distal region of a device in accordance with an alternate embodiment of the invention.

Referring now to FIG. 5, there is illustrated an alternate embodiment of a functional tip region 500. Functional tip region 500 comprises one energy delivery device 502 in a ring configuration. Conducting wire 504 covered with electrical insulation 506 is coupled to the energy delivery device 502, and energy delivery device 502 is positioned around the perimeter of a single opening 508 that provides a pathway between main lumen 510 and a patient's body. Another similar embodiment to functional tip region 500 comprises an active electrode in a partially annular shape (not shown).

In further embodiments, a functional tip may comprise multiple electrodes. Such electrodes may operate in a monopolar mode as with the embodiments detailed in FIGS. 2 and 5.

In order to measure pressure at the distal region 106 of the apparatus 102, an external pressure transducer 121 may be coupled to apparatus 102. For example, adapter 119 may be releaseably coupled to external tubing 123 that is coupled to external pressure transducer 121. In use, external tubing 123 may be flushed with saline to remove air bubbles. When apparatus 102 is positioned in a blood vessel in a body, pressure of fluid at distal region 106 exerts pressure through openings 109 on fluid within main lumen 200, which exerts pressure on saline in external tubing 123, which exerts pressure on external pressure transducer 121. The at least one opening 109 and lumen 200 provide a pressure sensing mechanism in the form of a pressure transmitting lumen for coupling to pressure transducer 121. External pressure transducer 121 produces a signal that varies as a function of the pressure it senses. External pressure transducer 121 may also be releaseably electrically coupled to a pressure monitoring system 125 that converts the transducer's signal and displays a pressure contour as a function of time. Thus, pressure may be optionally measured and/or recorded and, in accordance with one embodiment of a method aspect as described further herein below, used to determine a position of the distal region 106 in a patient's body. In those embodiments of apparatus 102 that do not comprise any lumens, a pressure transducer may be mounted at or proximate to distal region 106 and coupled to pressure monitoring system 125 via an electrical connection.

Figure 6:
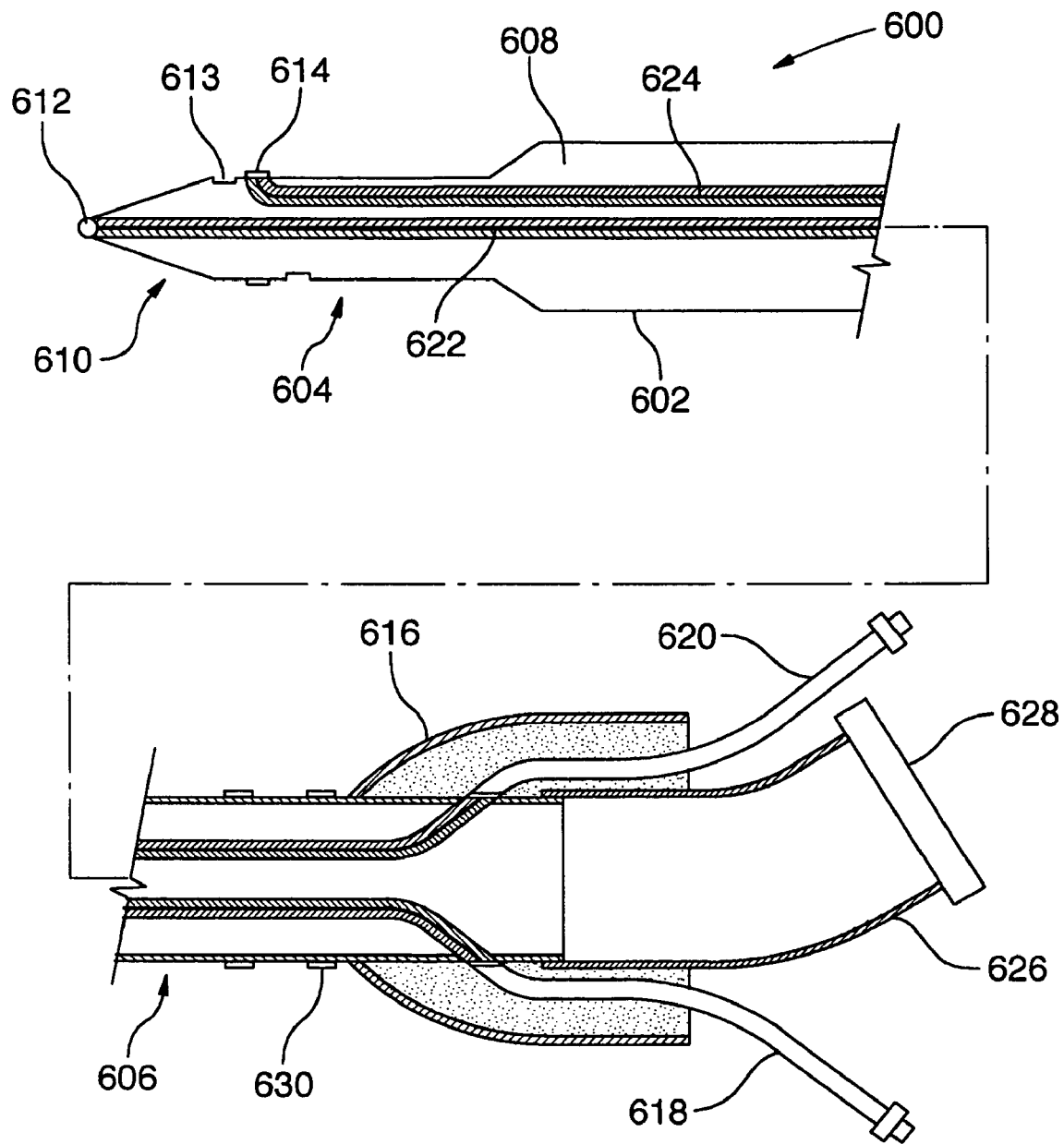
FIG. 6 illustrates a side cross-sectional view of an alternate embodiment of the device.

Referring now to FIG. 6, there is illustrated a side cross-sectional view of an alternate embodiment of apparatus 600 which operates in a bipolar mode. Apparatus 600 comprises an elongate member 602 having a distal region 604, and a proximal region 606. Elongate member 602 has at least one lumen 608 extending from proximal region 606 to distal region 604. In some embodiments, the outer diameter of elongate member 602 tapers down to distal region 604. In alternate embodiments the outer diameter of elongate member 602 remains substantially constant along its length.

Distal region 604 terminates at functional tip region 610. Functional tip region 610 comprises one energy delivery device 612 and one reference electrode 614. In an alternate embodiment comprising a kit including apparatus 600 and at least one of a sheath, such as sheath 800, and a dilator, such as dilator 910, a reference electrode may be located at the distal tip 912 of dilator 910 or at the distal tip 802 of sheath 800.

Both the energy delivery device 612 and reference electrode 614 can be configured in various shapes. These shapes include a spherical shape, a rounded shape, a ring shape, a semi-annular shape, an ellipsoid shape, an arrowhead shape, a spring shape and a cylindrical shape, among others. One or more radiopaque markings may be affixed to elongate member 602 to highlight the location of the transition from distal region 604 to the remainder of elongate member 602, or other important landmarks on apparatus 600. Alternately, the entire distal region 604 of apparatus 600 may be radiopaque. Distal region 604 may define at least one opening 613 in fluid communication with lumen 608.

In an alternate embodiment, the distal region 604 comprises a curve portion. Curve length may be about 4 cm (about 1.57") to about 6 cm (about 2.36") and the curve may traverse about 225 to about 315 degrees of the circumference of a circle. For example, the curve may be about 5 cm in length and may traverse about 270 degrees of the circumference of a circle. Such an embodiment may be useful to avoid unwanted damage to cardiac structures.

In some embodiments, the curve portion begins about 0.5 cm to about 1.5 cm proximal to energy delivery device 612, leaving an approximately 1 cm (about 0.39") straight portion in the distal region 604 of apparatus 600. This ensures that this initial portion of apparatus 600 will exit dilator 910 (see FIG. 9 below) without curving, enabling the operator to easily position the apparatus 600, for example, against a septum as described further below. This feature further ensures that the distal region 604 of apparatus 600 will not begin curving within the atrial septum.

Lumen 608 extends from proximal region 606 along elongate member 602 and through distal region 604 of apparatus 600. At least one opening 613 at the distal region 604 provides a pathway between lumen 608 and the environment surrounding distal region 604, such as a desired location within a patient's body. Openings 613 may be sufficiently dimensioned to easily aspirate blood to and through lumen 608 and to inject radiopaque contrast; however, openings 613 may be limited in number and dimension so that they do not compromise the structural integrity of distal region 604. In order to facilitate even distribution of contrast agent and to prevent pooling in lumen 608 at distal region 604, openings 613 may be dimensioned such that distally located openings are larger than proximally located openings. The location of openings 613 is as close to energy delivery device 612 as possible so that only a small portion of apparatus 600 is required to extend from dilator 910 and sheath 800 in order to measure pressure.

Proximal region 606 comprises a hub 616, an active connector cable 618, a reference connector cable 620, tubing 626 and an adapter 628. Hub 616 may comprise a curve direction or orientation indicator that is located on the same side of apparatus 600 as the curve in order to indicate the direction of the curve. Proximal region 606 may also have one or more depth markings 630 to indicate distances from energy delivery device 612, or other important landmarks on apparatus 600. Adapter 628 is configured to releaseably couple apparatus 600 to an external pressure transducer. Both active connector cable 618 and reference connector cable 620 may connect to an ECG interface unit.

Energy delivery device 612 may be coupled to an insulated conducting wire 622. Conducting wire 622 carries electrical energy from a generator to the energy delivery device 612. Conducting wire 622 also carries action potentials or voltage measured by energy delivery device 612 to an ECG recorder. Conducting wire 622 extends through main lumen 608 of apparatus 600. Conducting wire 622 extends along elongate member 602 from distal region 604 to proximal region 606 and is electrically coupled to active connector cable 618 within hub 616.

Reference electrode 614 may be coupled to an insulated conducting wire 624. Conducting wire 624 carries electrical energy from a patient to a generator. Conducting wire 624 also carries action potentials or voltage measured by reference electrode 614 to an ECG recorder. Conducting wire 624 extends through main lumen 608 of apparatus 600. Conducting wire 624 extends along elongate member 602 from distal region 604 to proximal region 606 and is electrically coupled to reference connector cable 620 within hub 616.

In the bipolar mode, RF energy is delivered through energy delivery device 612 (i.e. active electrode 612), and returns to the generator through reference electrode 614. The use of an active and a reference electrode attached to apparatus 600 eliminates the need for a grounding pad to be attached to the patient. With an active-return electrode arrangement at functional tip region 610, action potentials or voltage measured by the energy delivery device 612 are with reference to the ground or reference electrode 614 located at the function tip region 610. The ECG recorder assigns a zero potential value to the reference electrode 614. A zero potential or ground electrode within the ECG recorder or placement of a ground electrode on the patient is not required and a higher fidelity recording may be facilitated.

Figure 7:
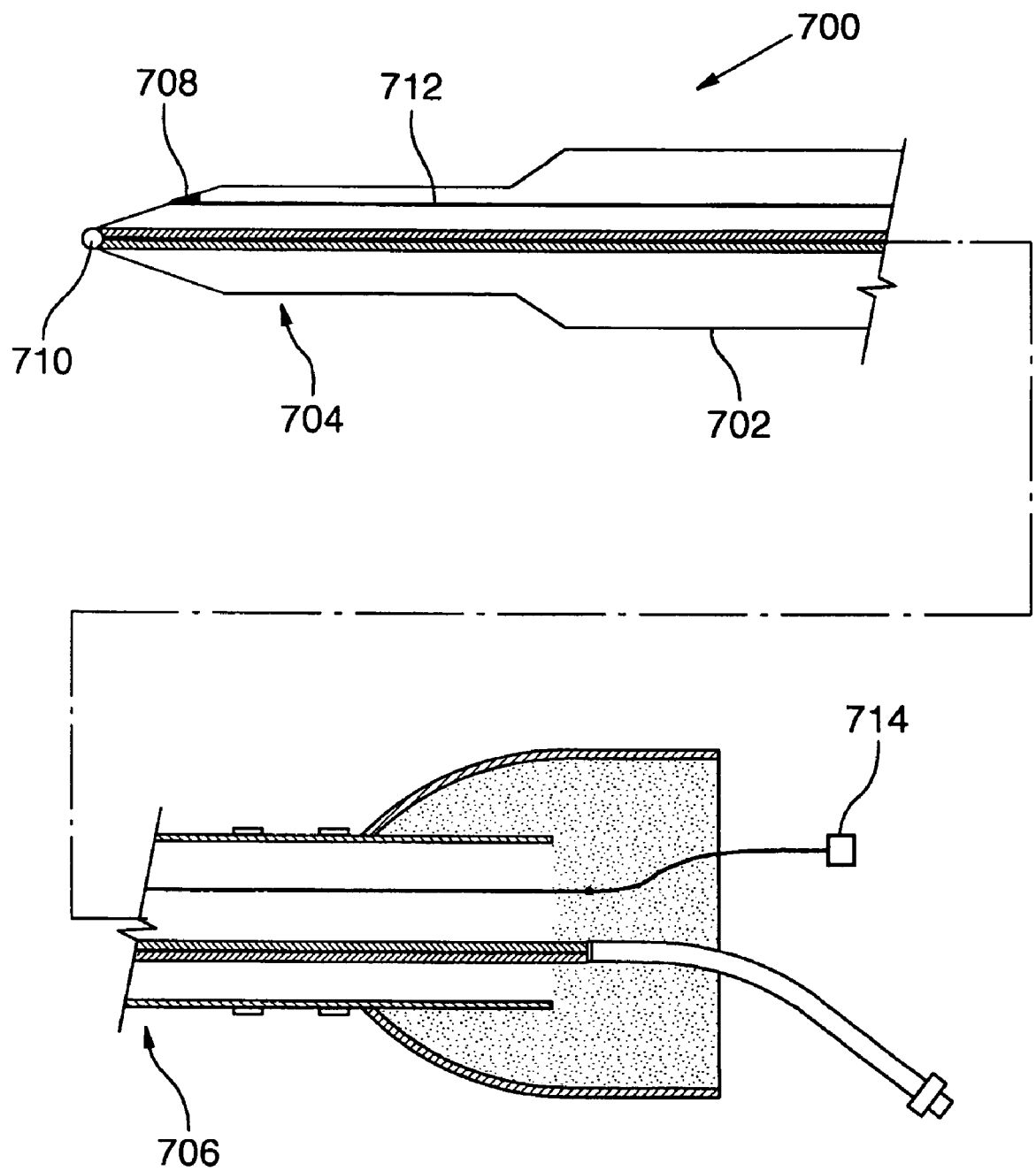
FIG. 7 illustrates a side cross-sectional view of an alternate embodiment of the device.

Referring now to FIG. 7, there is illustrated a side cross-sectional view of proximal 706 and distal 704 regions of an alternate embodiment of an apparatus 700 that does not require an external pressure transducer. In this embodiment the pressure sensing mechanism comprises an on-board pressure transducer 708 coupled by an adhesive to elongate member 702 at distal region 704. The pressure transducer 708 is configured at distal region 704 such that pressure close to energy delivery device 710 can be transduced. The on-board pressure transducer 708 is electrically coupled to a pressure communicating cable 712 to provide power to transducer 708 and to carry a pressure signal to proximal region 706 of the apparatus 700. Pressure communicating cable 712 terminates in a monitoring system connector 714 that is configured to be releaseably coupled to a pressure monitoring system. The pressure monitoring system converts the pressure signal and displays pressure as a function of time. In the embodiment of FIG. 7, a main lumen such as the main lumen 200 of FIG. 2 is not required for fluid communication with an external pressure transducer 121 (shown in FIG. 1). In addition, this embodiment does not require openings, such as openings 109 shown in FIG. 1, at distal region 704 for fluid communication with a main lumen. However, a lumen with openings may be provided for injecting or aspirating fluids, if desired.

Optionally, to measure and record ECG at the distal region of the apparatus 102, ECG recorder 126 is connected to apparatus 102 through the ECG interface unit 120. Hub 114 is coupled to catheter connector cable 116 that is coupled to connector 118 as shown in FIG. 1. Connector 118 is attached to ECG Interface unit 120. When apparatus 102 is maneuvered in a patient's body, particularly in a heart, electrical action potentials or voltage detected by energy delivery device 112 are transmitted along conducting wire 202 and catheter connector cable 116, through ECG interface unit 120 and are captured and displayed on ECG recorder 126. Different locations in a heart are at different electric potentials and thus the voltage measured varies as the position of energy delivery device 112 is varied. A conversion circuit within ECG recorder 126 may be used to convert the measured voltage or potential into a picture or waveform recording that varies as a function of time.

Sheaths and Dilators

Figure 8A:
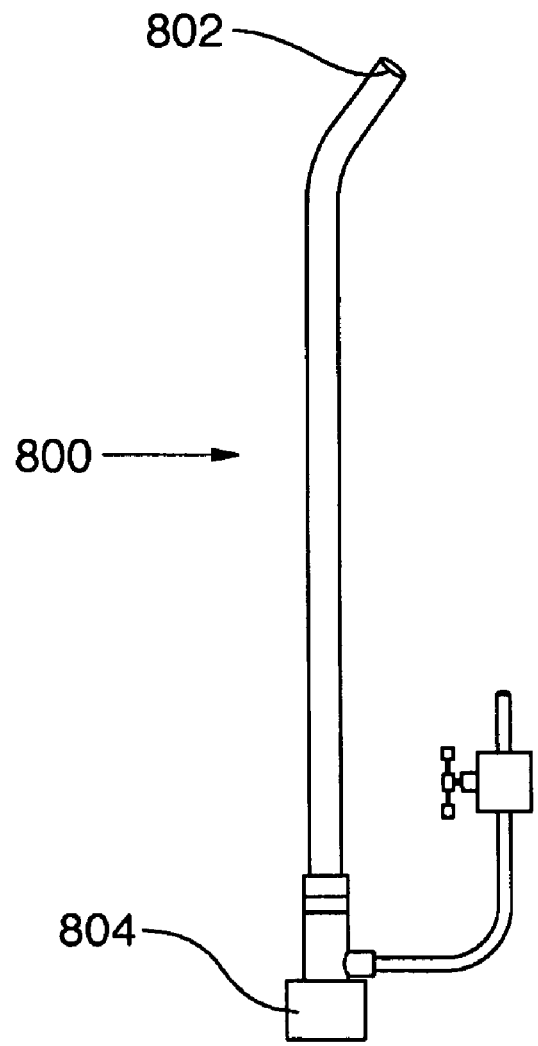
FIGS. 8A and 8B illustrate two possible embodiments of a guiding sheath.
Figure 8B:
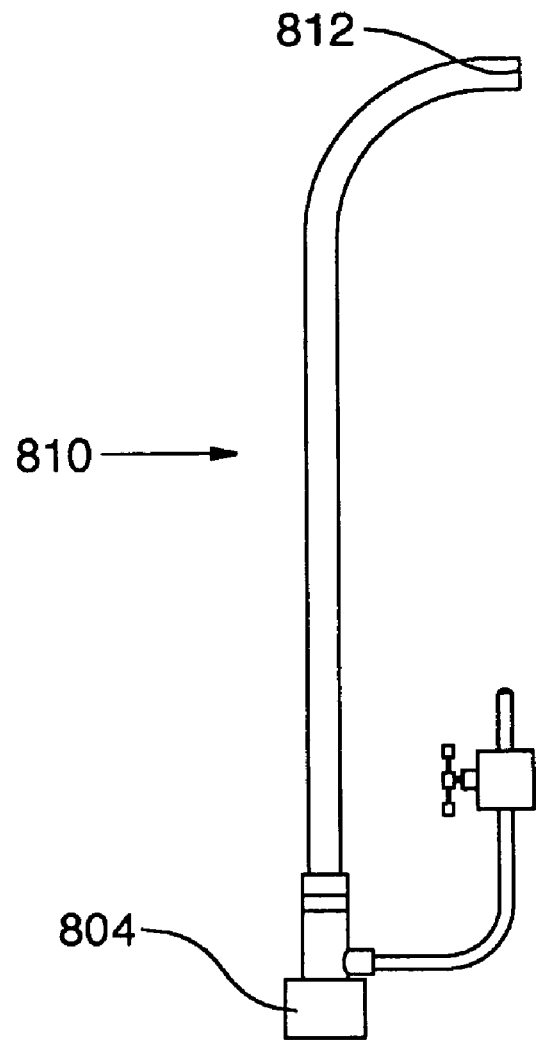

In order to create a perforation in the heart, apparatus 102 is delivered to the heart using a guiding sheath and dilator known to those of ordinary skill in the art. FIGS. 8A and 8B show alternate embodiments 800 and 810 of a guiding sheath. Guiding sheaths 800 and 810 both comprise distal tips (802 and 812, respectively) and proximal hubs 804. Distal tip 802 is configured and shaped for approaching the heart via the inferior vena cava (IVC) while distal tip 812 is configured and shaped for approaching the heart via the superior vena cava (SVC). Distal tip 812 may comprise a curve of between about 45 degrees to about 90 degrees with a relatively short radius such that, when sheath 812 is advanced into the left atrium, the entire curve may sit within the left atrium. Then, through rotating the sheath shaft, the orientation of distal tip 812 may be rotated about its lateral axis. One purpose of the sheath is to provide a conduit for any catheters or other devices that may be introduced therethrough into a patient's heart and to orient the devices such that it facilitates their use. Thus, various curves would be useful depending on the final desired position of the sheath within the patient's heart. The curve of distal tip 812 shown in FIG. 8B may be particularly useful for mitral valve access for balloon valvuloplasty and/or RF ablation of the left side of the heart. Sheaths 800 and 810 may both define a lumen through which a dilator or other device may be delivered. In addition, sheaths 800 and 810 may comprise one or more radiopaque markers or reference electrodes.

Figure 9:
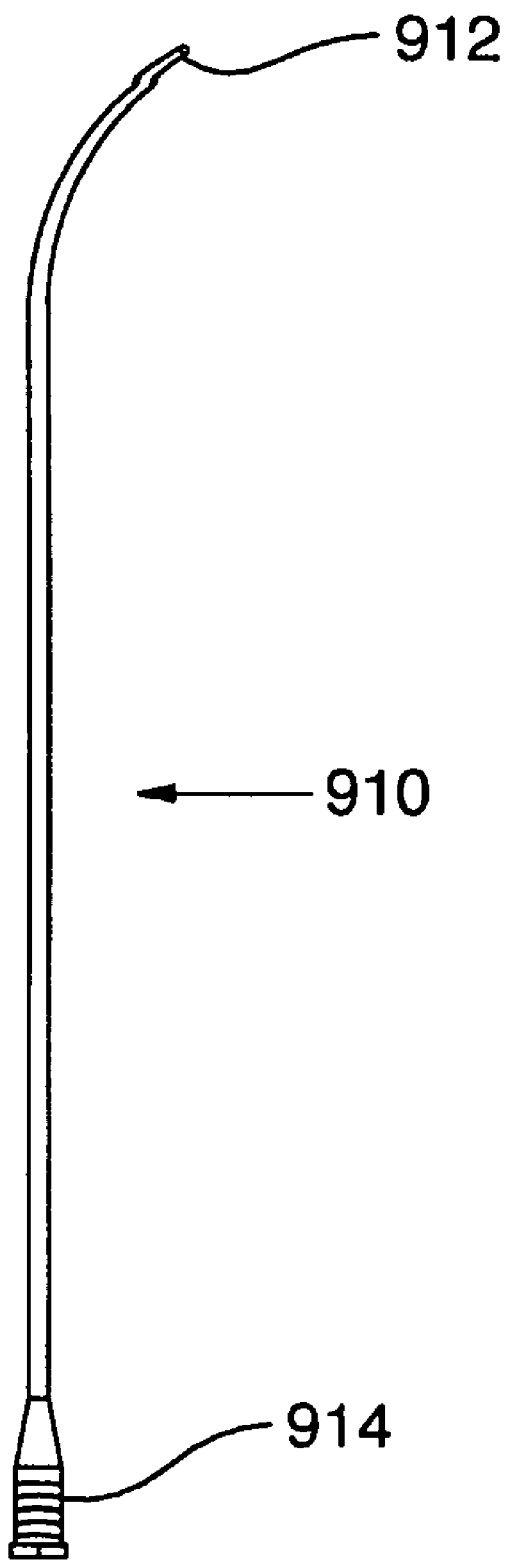
FIG. 9 illustrates one embodiment of a dilator.

FIG. 9 illustrates a dilator 910 comprising a tip 912 at the distal end thereof and a proximal hub 914. Dilator 910 may be useful when approaching the heart via the IVC due to the shape thereof. Dilator 910 may have one or more radiopaque markers or reference electrodes. In addition, dilator 910 may define a lumen sized to allow for passage of said dilator over a guidewire or for delivery of Apparatus 102 through said dilator.

Figure 10A:
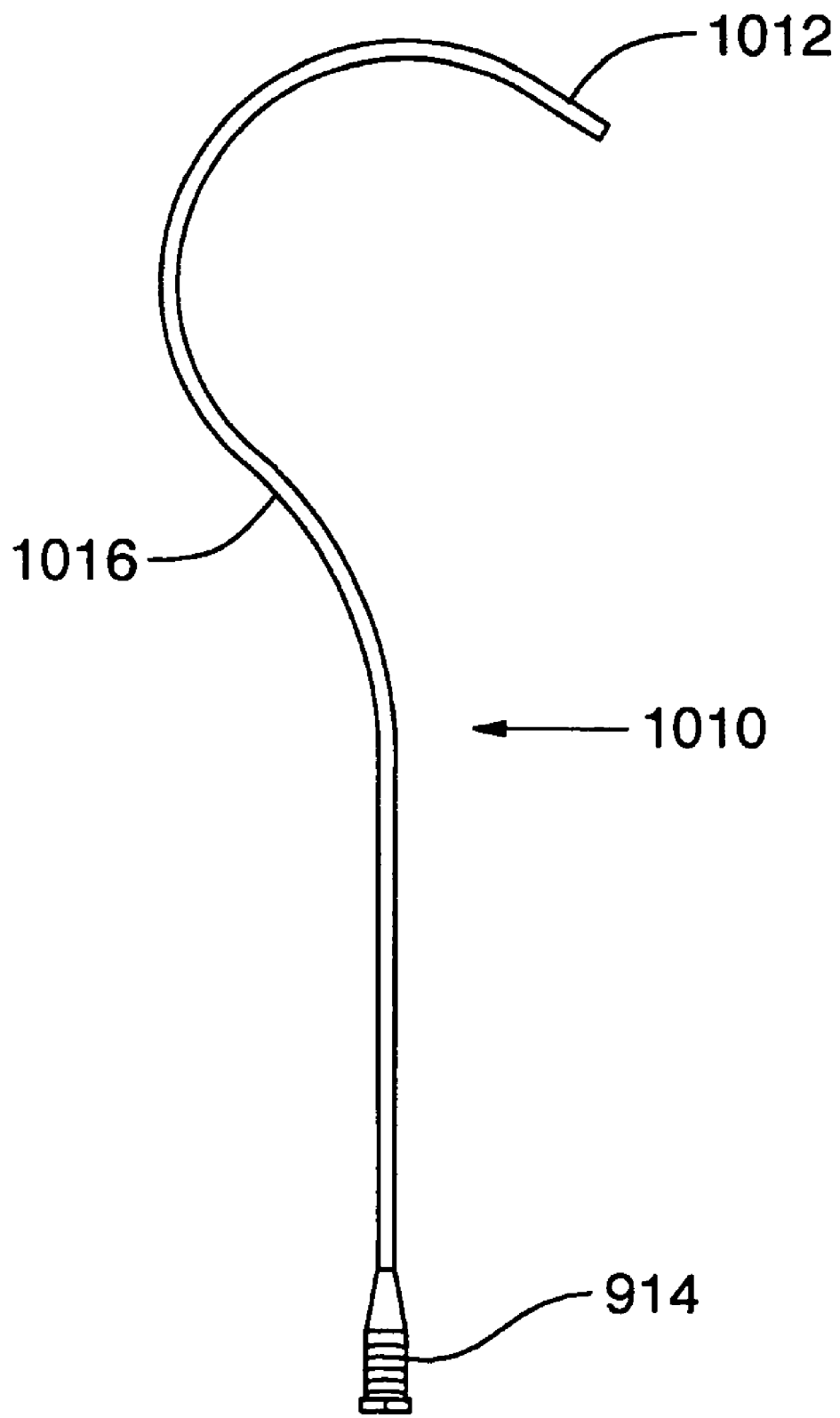
FIGS. 10A, 10B and 10C illustrate alternate embodiments of a dilator.
Figure 10B:
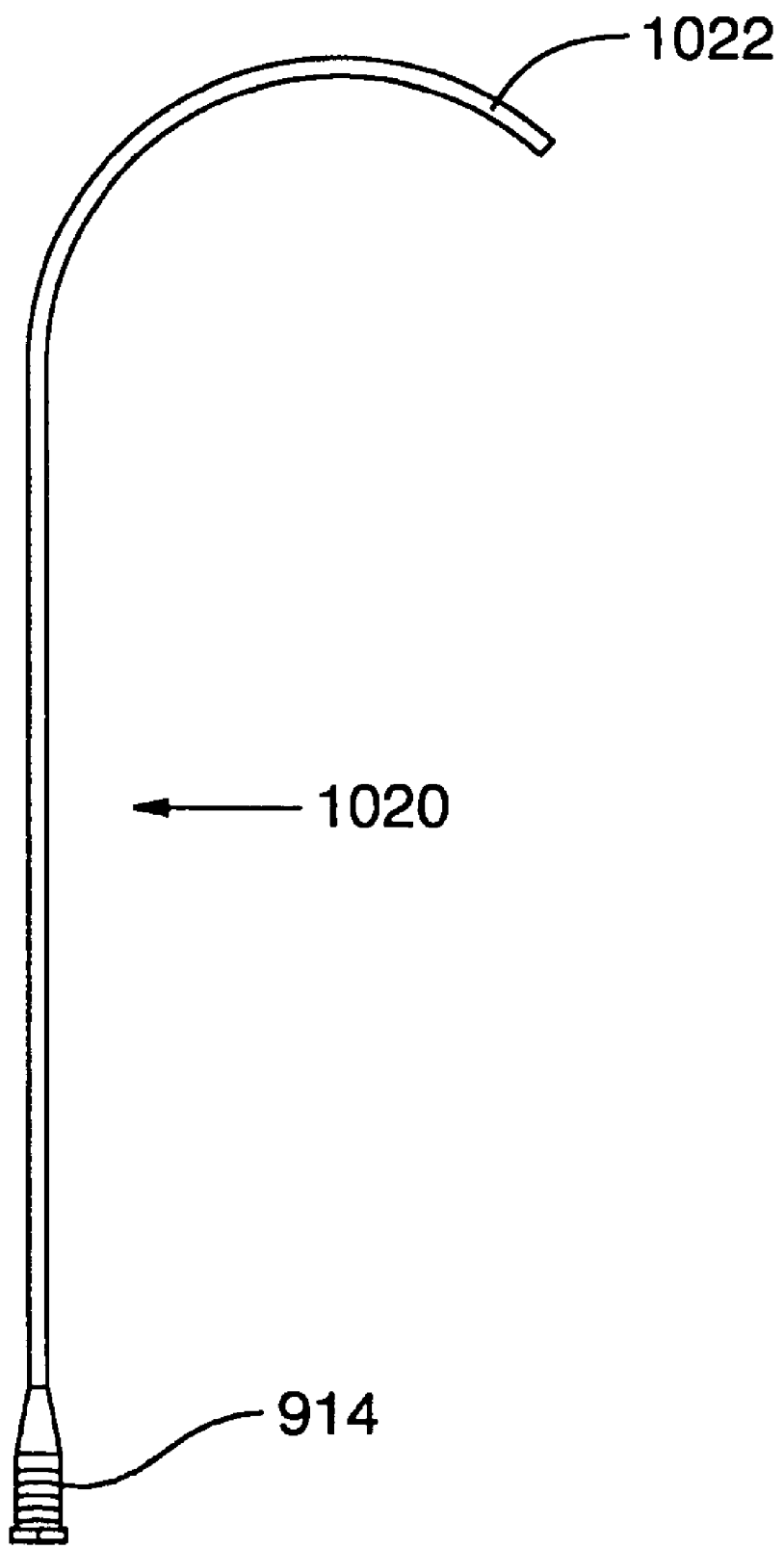
Figure 10C:
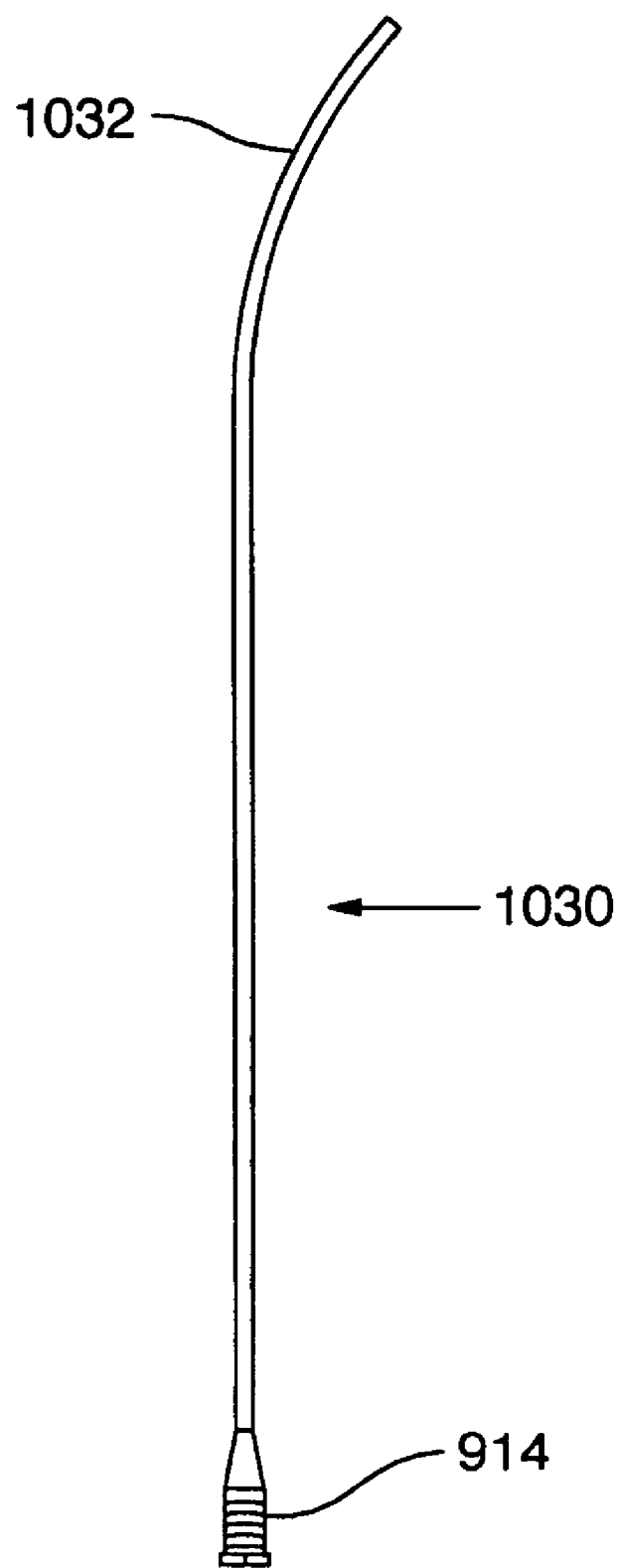

FIGS. 10A, 10B and 10C show alternate embodiments of dilator shapes that may be useful when approaching the heart via the SVC. As illustrated in FIGS. 13A, 13B, 14A and 14B below, and as will be discussed in greater detail, performing a trans-septal perforation utilizing a sheath and dilator typically involves several steps, including positioning the energy delivery device against the septum and advancing the dilator and/or sheath across the septum. Each of these steps may require the dilator to be configured in a specific manner in order to perform the desired function. For example, in order to position the energy delivery device against the septum for perforation, it may be desirable to position the energy delivery device at an angle of about 80 to about 100 degrees relative to the surface of the septum. In some embodiments, the energy delivery device should be positioned substantially perpendicularly to the septum prior to perforation. In order to achieve this results, a dilator as shown in FIG. 10A (1010) or 10B (1020) may be employed. Both of these dilators comprise distal tips (1012 and 1022, respectively) that are shaped so as to position the energy delivery device appropriately against the septum when the heart is approached via the SVC.

Once the perforation is created, the dilator and/or sheath may be advanced across the perforation into the left atrium. In order to achieve this most efficiently, it may be advantageous to employ a dilator that can transmit a longitudinal force applied at a proximal end thereof into a force directed at the perforation in order to dilate the perforation sufficiently. In some embodiments, a dilator 1030, as illustrated in FIG. 10C, may be used. Dilator 1030 comprises a distal tip 1032 with a relatively gentle curve (less than 90 degrees) that lends itself to transmitting mechanical force applied at a proximal end of the dilator to advance the dilator through the perforation. In this configuration, the apparatus comprising the energy delivery device may serve to act as a rail to prevent dilator 1030 from slipping down the septum. Alternatively, dilator 1010 may be used to advance the dilator and/or sheath through the perforation. In such an embodiment, as a longitudinal force is applied at a proximal end of the dilator, the dilator and/or sheath may flex and push against the free wall of the right atrium, thereby providing back support and directing force towards the septum. The specific curve used in this embodiment may depend on the specific geometry of the right atrium of the patient. Any of dilators 1010, 1020 and 1030 may comprise hubs 914 as well as radiopaque markers and/or reference electrodes. In alternate embodiments, one or more of the sheath and dilator may be steerable and/or articulating, whereby a shape of the sheath or dilator may be adjusted during the course of the procedure. This may allow for a user to define the precise curve required for each step of the trans-septal perforation.

Figure 11:
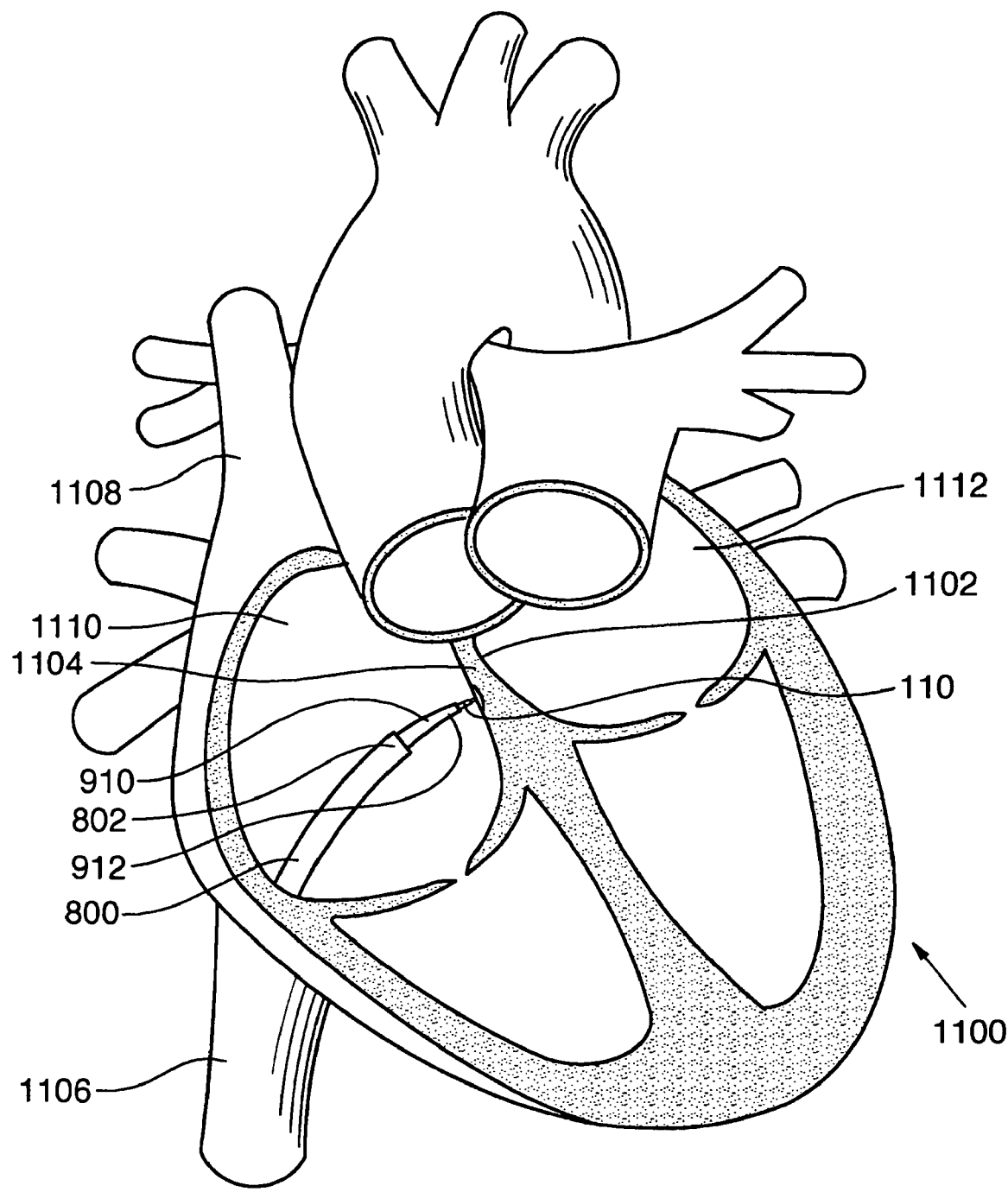
FIG. 11 illustrates a first position of one embodiment of the present invention within a patient's heart.
Figure 13A:
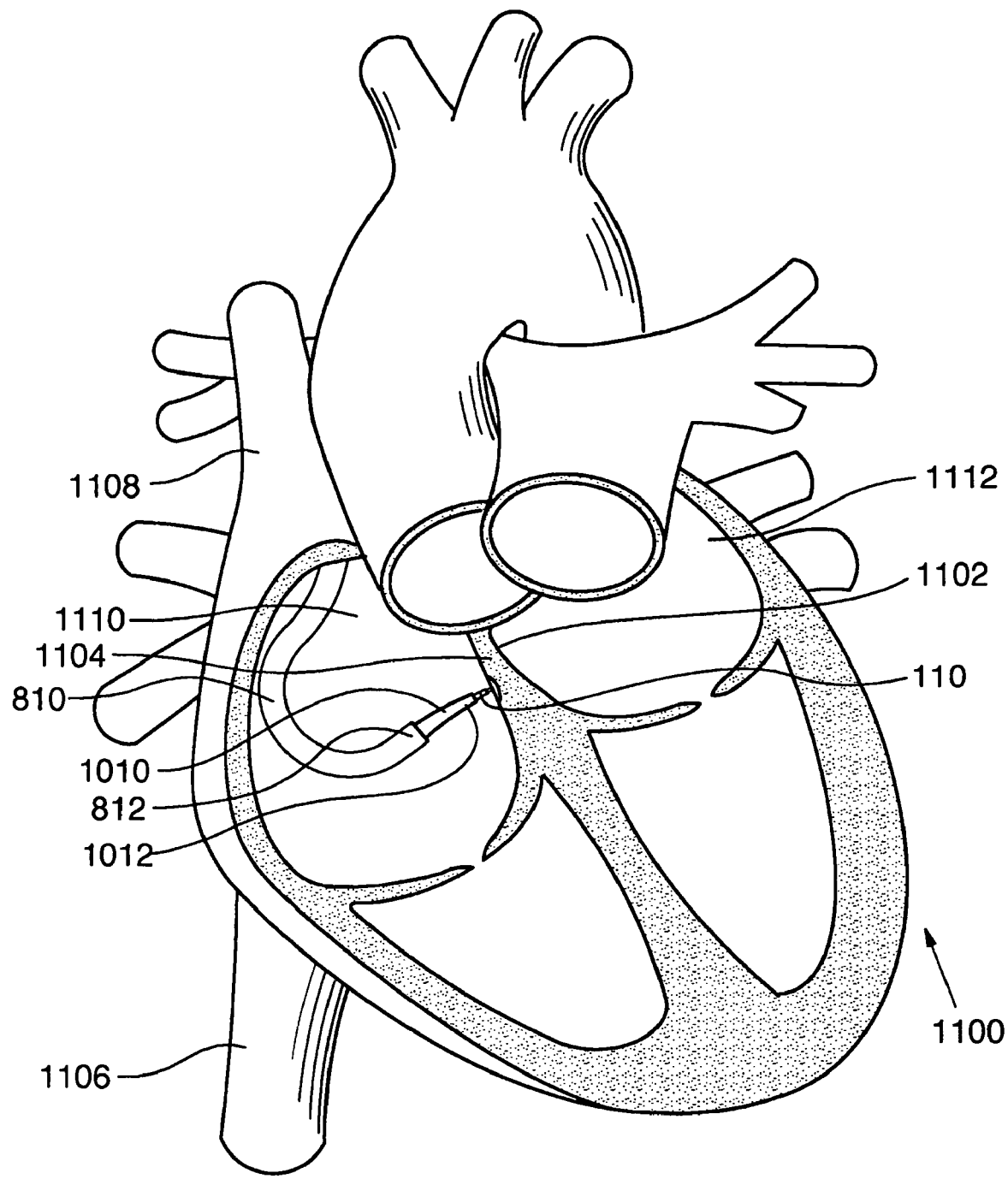
FIGS. 13A and 13B illustrate first positions of alternate embodiments of the present invention within a patient's heart.
Figure 13B:
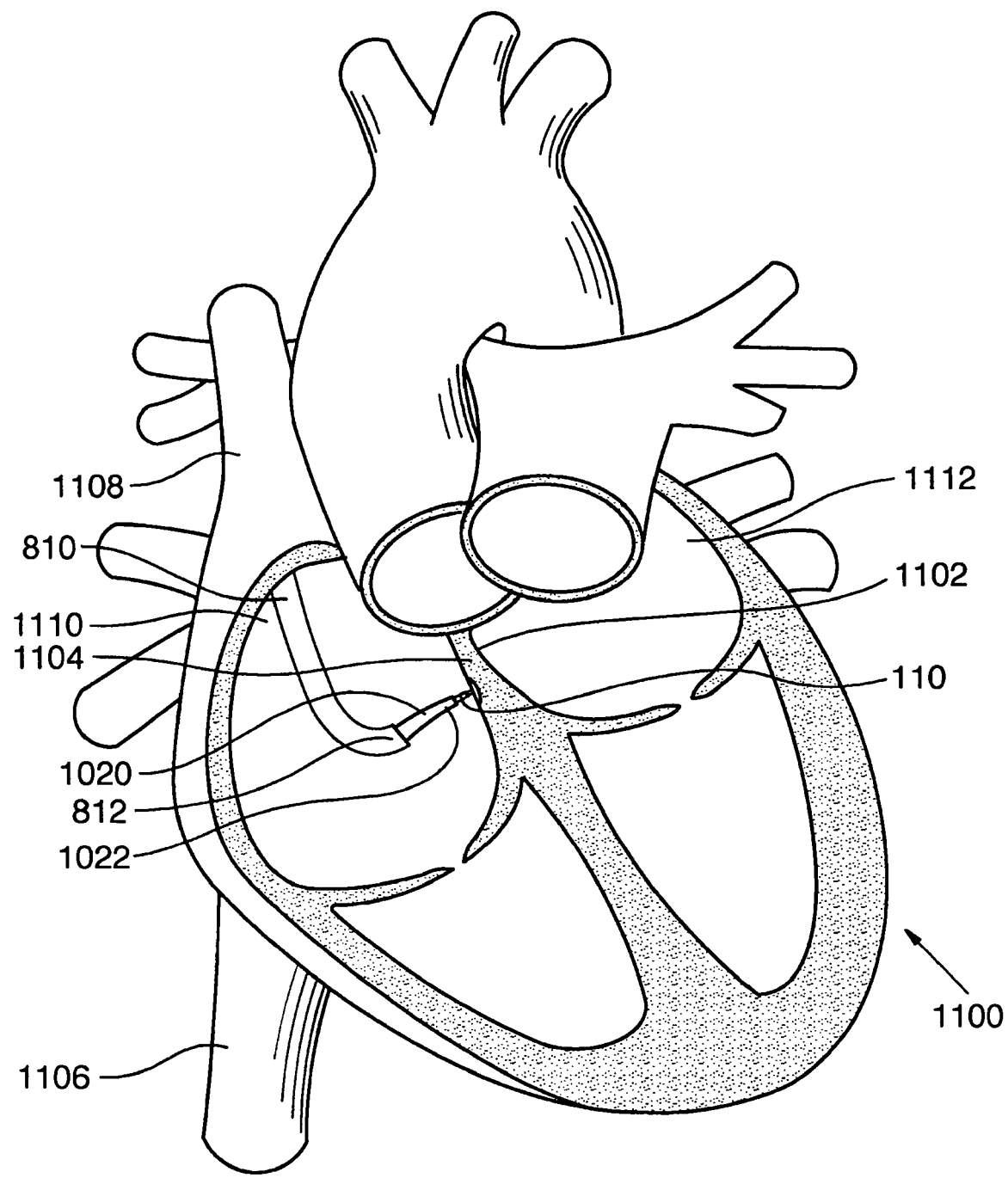
Figure 14A:
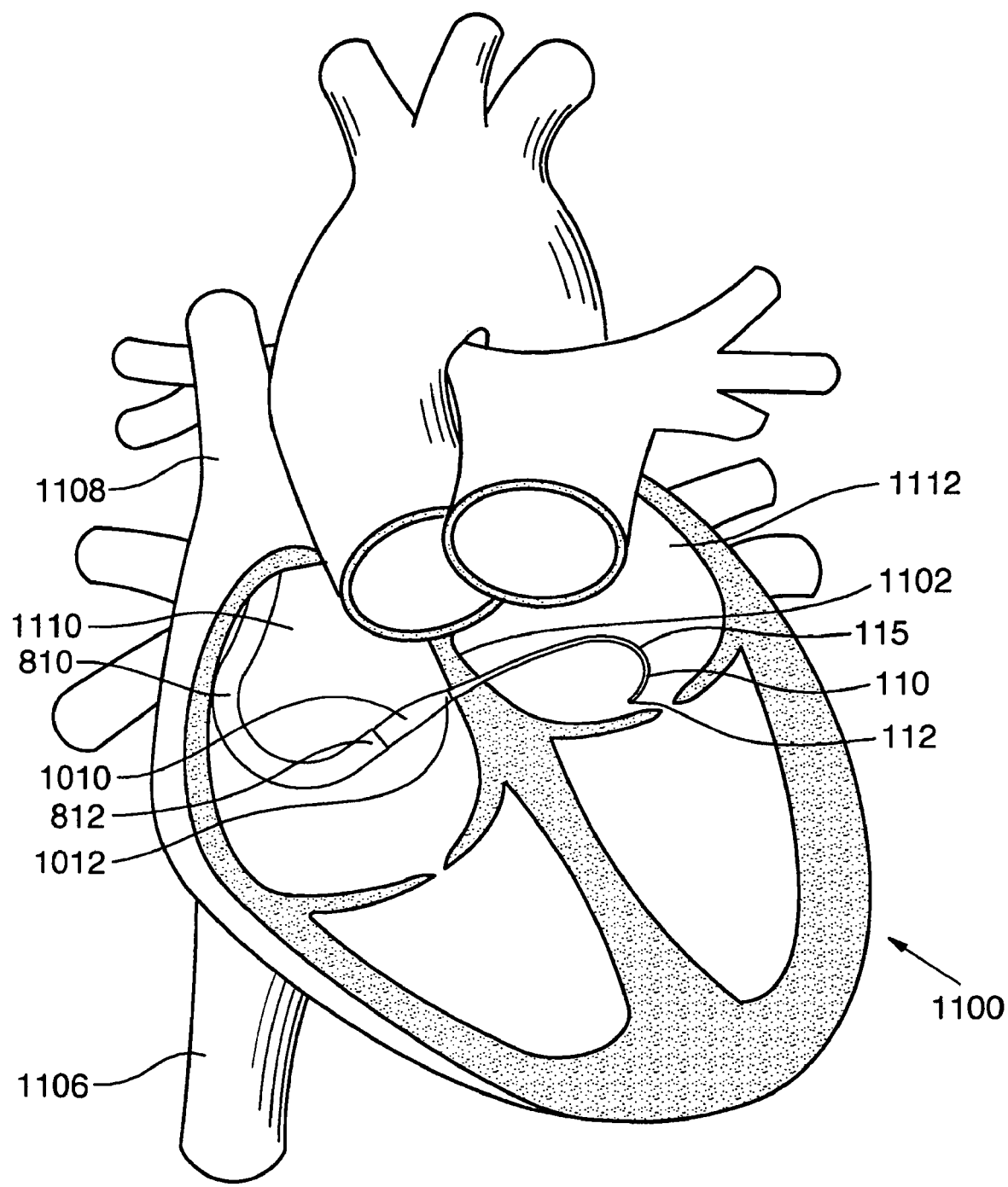
FIGS. 14A and 14B illustrate second positions of alternate embodiments of the present invention within a patient's heart.
Figure 14B:
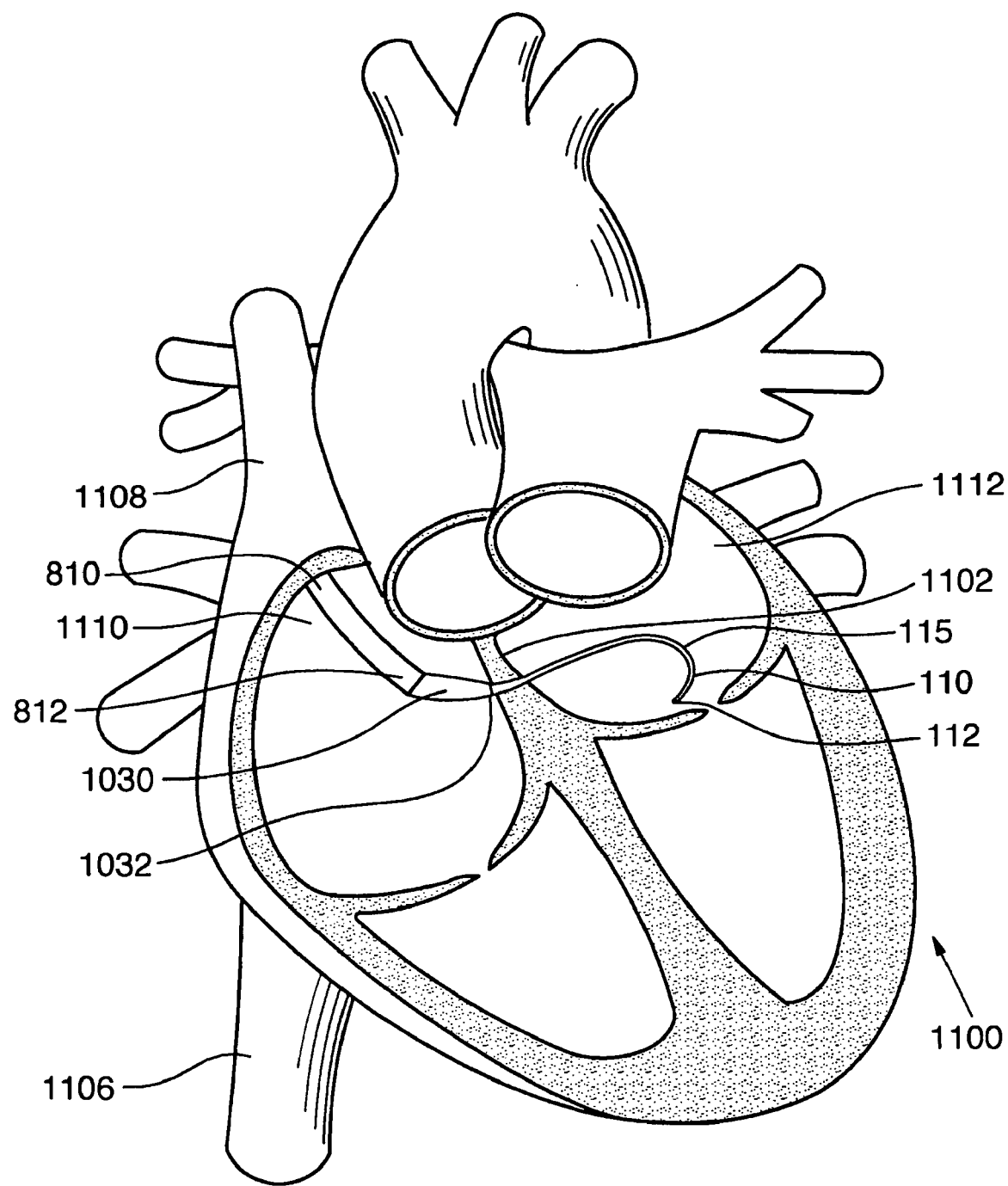

Referring now to FIGS. 11 and 12 there is illustrated Apparatus 102 inserted through dilator 910 and sheath 800 within a heart 1600 of a patient. In these figures, the heart has been approached via the inferior vena cava. FIGS. 13 and 14 provide illustrations of apparatus 102 inserted into the heart via the superior vena cava. FIGS. 13A and 14A show apparatus 102 inserted through dilator 1010 while FIGS. 13B and 14B show apparatus 102 inserted through dilators 1020 and 1030, respectively. In all of FIGS. 13 and 14 the dilators are inserted within sheath 810.

Method

Broadly speaking, embodiments of the present invention provide a method of surgical perforation via the delivery of electrical, radiant or thermal energy. They method may typically involved at least the following steps: introducing an apparatus comprising an energy delivery device into a patient's heart via the patient's superior vena cava; positioning the energy delivery device at a first location adjacent the material to be perforated; and perforating the material by delivering energy via the energy delivery device; wherein the energy is selected from the group consisting of electrical energy, radiant energy and thermal energy.

Figure 16A:
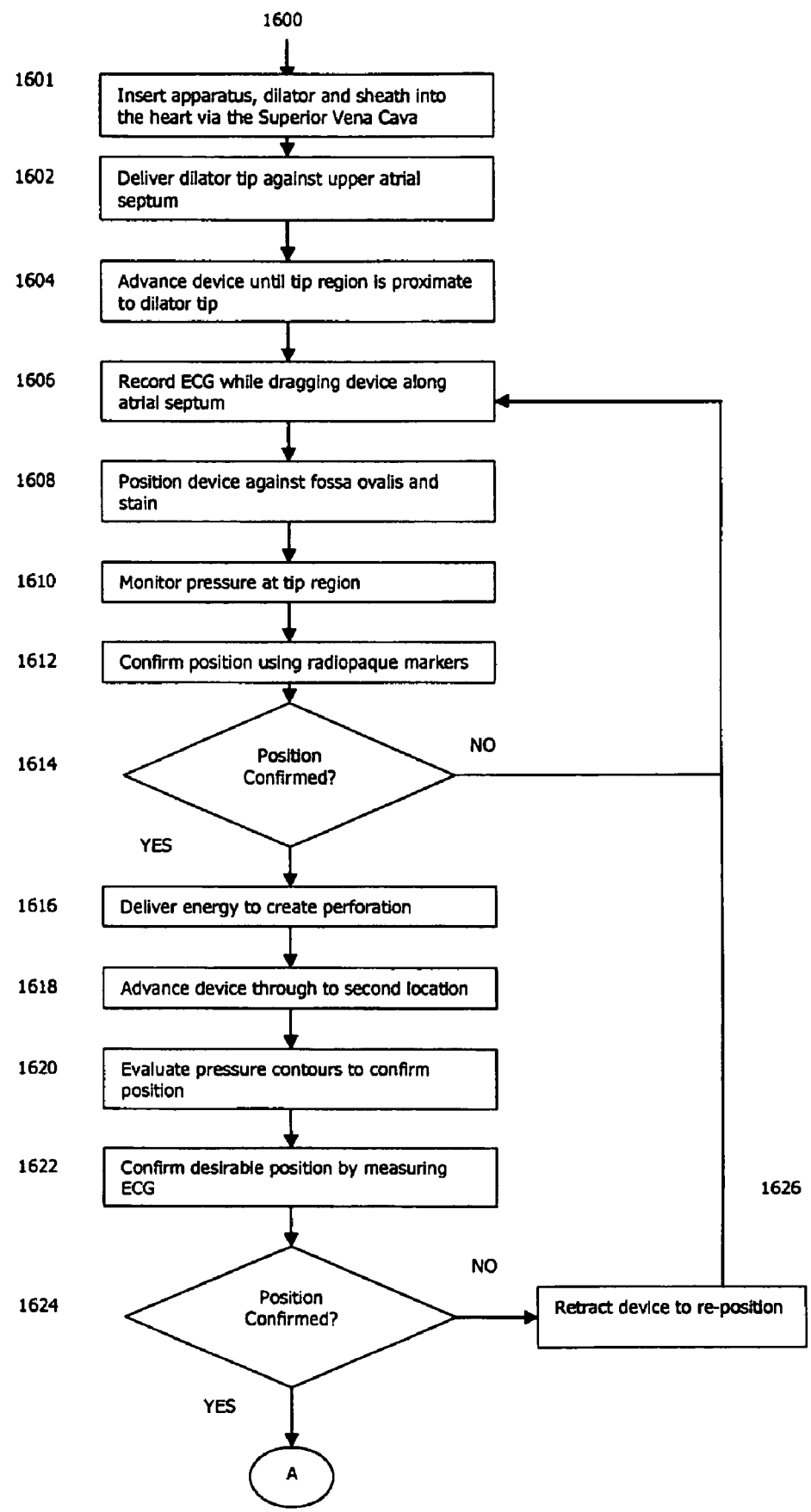
FIGS. 16A and 16B illustrate a flow chart of a trans-septal perforation method in accordance with an embodiment of this invention.
Figure 16B:
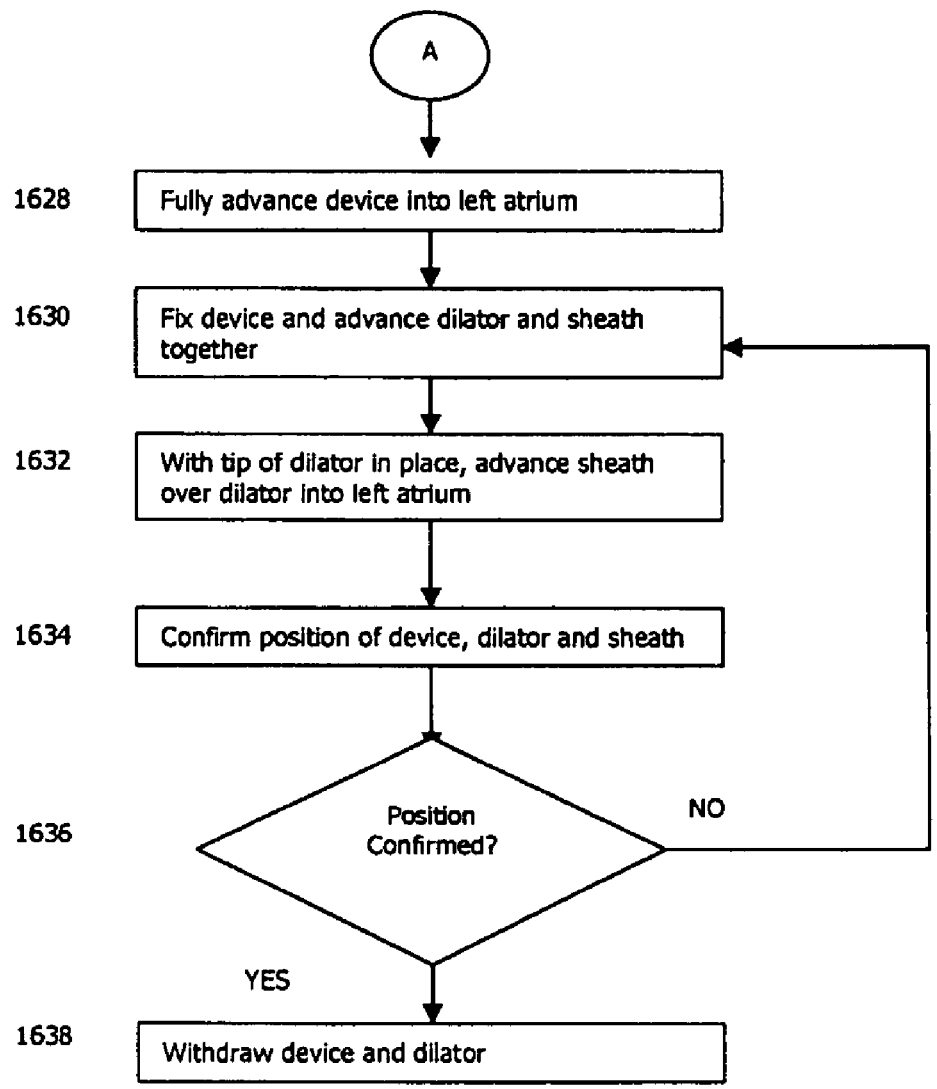

As one specific example of this method, operational steps 1600 for a method of creating a trans-septal perforation in accordance with an embodiment of the invention are outlined in flowchart form in FIGS. 16A and 16B. In accordance with a method aspect of the invention for creating a trans-septal perforation, the apparatus, dilator and sheath may be introduced into the heart via the SVC (step 1601). Alternatively, the heart may be accessed via the IVC, as shown in FIGS. 11 and 12. In order to deliver the tip of the dilator against the upper region of the atrial septum 1102 (step 1602) a guiding sheath and dilator with a lumen sufficient to accommodate the outer diameter of the Apparatus 102 may be introduced into a patient's vasculature. In alternate embodiments of the present invention, the procedure may be performed without a sheath and/or dilator. In either case, the method comprises steps of introducing one or more devices and/or apparatuses into the patient's vasculature and advancing the devices/apparatuses through the vasculature into the patient's heart. Access to the vasculature may be achieved though a variety of veins large enough to accommodate the guiding sheath and dilator and the present invention is not limited in this regard. The guiding sheath and dilator may be advanced together through the vasculature. In one embodiment, illustrated in FIGS. 11 and 12, they approach the heart from the Inferior Vena Cava (IVC) 1106 and proceed into the Superior Vena Cava (SVC) 1108 of the heart 1100. In accordance with this embodiment, access to the vasculature may be gained via the femoral vein. The sheath and dilator may then be withdrawn from the SVC 1108, into the right atrium 1110. In another embodiment, illustrated in FIGS. 13-14, the guiding sheath and dilator approach the heart via the SVC and proceed directly into the right atrium. In accordance with this alternate embodiment, access to the vasculature may be gained via one or more of the subclavian vein, the brachial vein, the axillary vein and the jugular vein.

Contrast agent may be delivered through the dilator while positioning the dilator and sheath along the atrial septum 1102. The sheath and dilator are now positioned within the right atrium 1110 of heart 1100 so that the tip of the dilator is located against the upper region of the atrial septum 1102 (step 1602).

Once the tip of the dilator is in position against the upper region of the atrial septum 1102, apparatus 102 can be advanced through the dilator until functional tip region 110 is located distally to the tip of the dilator (step 1604). Distal region 106 of apparatus 102 is pliable so that the curve 115 straightens out within the dilator and takes on the shape of the dilator as it is advanced to the atrial septum 1102. Apparatus 102 is coupled to the ECG recorder 126 and an ECG tracing monitored through energy delivery device 112, known to those of ordinary skill in the art, may be shown on ECG recorder 126. The technique for obtaining an ECG tracing was previously described. In some embodiments, apparatus 102, the dilator and the sheath are now dragged along the atrial septum 1102 while monitoring the ECG tracing on the ECG recorder 126 (step 1606). Confirmation of the position of energy delivery device 112 of apparatus 102 against the fossa ovalis 1104 is made once a distinctive change in the ECG tracing on ECG recorder 126 is observed. This is due to energy delivery device 112 advancing over the region of the fossa ovalis 1104 which is membranous in comparison with the muscular atrial septum 1102.

H. Bidoggia et. al. (1991) who performed experiments on the usefulness of the intracavitary ECG (recorded using a trans-septal needle) in the localization of the fossa ovalis states that when the tip of the needle was laid against the fossa ovalis floor, the endoatrial electrocardiogram registered a slight or no injury curve, even when the pressure was sufficient to perforate the septum. On the contrary, pressure on any other areas of the muscular septum or atrial walls elicited a bizarre monophasic injury curve. This shows that the ECG signal recorded by a surgical device while on the membranous fossa ovalis will be damped in comparison with the ECG signal recorded on the muscular areas of the atrial septum or atrial walls. This difference in ECG signal may be useful in locating the region of the fossa ovalis as a surgical device is positioned within a heart. ECG may be displayed on a screen and/or printed on a chart, for example. The distinctive change may be signaled for observation as well using an alarm such as an audible or visual signal.

The position of apparatus 102 may also be confirmed by monitoring pressure at the functional tip region 110 (step 1610). Apparatus 102 is coupled to external pressure transducer 121 and a right atrial pressure contour, known to those of ordinary skill in the art, may be displayed on monitoring system 125. The technique for obtaining a pressure contour was previously described.

The position of functional tip region 110 and energy delivery device 112 may be additionally confirmed using an imaging modality such as fluoroscopy. Under fluoroscopy, radiopaque markings associated with distal region 106 of apparatus 102 may be aligned with a radiopaque marker located distally on the dilator such that functional tip region 110 of apparatus 102 is located at the fossa ovalis 1104. Alternately, radiopaque markings associated with distal region 106 of apparatus 102 may be aligned with a radiopaque marker located distally on the sheath such that functional tip region 110 of apparatus 102 is located at the fossa ovalis 1104 (step 1612).

In some embodiments, radiopaque contrast agent or dye delivered through apparatus 102 will be directed through the openings 109 in functional tip region 110 into the tissue of the fossa ovalis 1104 in order to stain the tissue and make it more visible under radiographic imaging (step 1608). Using fluoroscopy, the stained region of the fossa ovalis 1104 can be seen as a dark patch in contrast to the atrial septum 1102, which appears as a lighter color. Functional tip region 110 may now be easily directed towards the fossa ovalis 1104. In embodiments whereby the heart is approached via the SVC (for example, FIGS. 13A and 13B), one or more of the dilator, sheath and apparatus may be shaped and or configured such that, upon positioning the apparatus within the right atrium 1110, functional tip region 110 may be positioned at an angle of about 80 degrees to about 100 degrees relative to the fossa ovalis 1104. In further embodiments, functional tip region 110 may be positioned substantially perpendicularly relative to the fossa ovalis 1104. Such a position may be achieved, for example, by using dilators 1010 or 1020, as shown in FIGS. 13A and 13B.

The position of functional tip region 110 of apparatus 102 is evaluated and if the desired position is not confirmed (step 1614, No branch), step 1606 may be repeated. If confirmed (step 1614, Yes branch), energy may be delivered to create the perforation. For example, generator 128 may be activated and RF energy may be delivered through apparatus 102 to make a perforation (step 1616). As mentioned above, the perforation may alternatively be created using radiant (e.g. laser) or thermal energy.

Referring to FIGS. 12 and 14, functional tip region 110 of apparatus 102 is thereafter advanced through the perforation and into a second location (step 1618). Advancement may be monitored under fluoroscopy using radiopaque markings on the distal region 106 of apparatus 102. In some embodiments, the second location is the left atrium 1112 of the heart. The distal region 106 of apparatus 102 is advanced incrementally into the left atrium 1112 through the dilator, for example, in about 1 cm (about 0.39") increments. After the first 1 cm of distal region 106 of apparatus 102 has been advanced out of the dilator across the atrial septum 1102, into left atrium 1112, the curve portion 115 of distal region 106 of apparatus 102 establishes its curved shape within the left atrium 1112. In other words, the distal tip of apparatus 102 may be directing in a desired direction, for example away from cardiac structures, following perforation of the septum. An orientation indicator located on apparatus 102 may be monitored in order to determine the direction of the distal tip of apparatus 102. The position of depth markings 113 of apparatus 102 relative to the proximal hub of the dilator can be used as a guide. Additionally, advancement of perforating apparatus 102 can be controlled by monitoring radiopaque markings on the distal region 106 of apparatus 102 under fluoroscopy. When the openings 109 on distal region 106 of apparatus 102 are located in the left atrium 1112, the evaluation of pressure contours from the left atrium via pressure transducer 121 (step 1620) can be performed. Apparatus 102 may remain coupled to external pressure transducer 121 so that a pressure contour at the second location can be measured and/or monitored confirming the desired location of the distal region following the perforation.

Additionally, when the distal region 106 of apparatus 102 is located in the left atrium 1112, the evaluation of the ECG tracing (step 1622) can be performed. Apparatus 102 remains coupled to ECG recorder 126 so that an ECG tracing at the second location can be monitored. After successful perforation, a left atrial pressure contour known to those of ordinary skill in the art, will be shown on monitoring system 125. In addition, a left atrial ECG tracing, known to those of ordinary skill in the art, will be shown on the ECG recorder 126. In the event that at least one of the imaging, pressure contours and ECG tracings show that the perforation has been made in an undesirable location (step 1624, No branch), apparatus 102 may be retracted into the right atrium 1110 (step 1626) and may be repositioned for another perforation attempt (step 1606). If the perforation is successfully made in the correct location (step 1624, Yes branch), distal region 106 of apparatus 102 may be further advanced through the perforation. In some embodiments, when apparatus 102 is fully inserted into the dilator, hub 114 of the apparatus 102 will be flush against the proximal hub of the dilator, and no depth markings 113 of apparatus 102 will be visible (step 1628, FIG. 16B). When fully inserted, apparatus 102 provides sufficient support to permit the dilator to be advanced over it through the perforation.

The dilator may be advanced through the perforation by applying a longitudinal force to the proximal end of the dilator. If the heart has been approached via the IVC, this longitudinal force may directly advance the dilator through the perforation. However, in some embodiments whereby the heart has been approached via the SVC, applying a longitudinal force may push the dilator down along the septum rather than through the perforation. In such embodiments, the dilator may be designed in such a way so that application of a longitudinal force onto a proximal end of the dilator may advance the distal end of the dilator through the perforation. For example, in FIG. 14A, dilator 1010 is shaped such that application of a longitudinal, downward force onto a proximal end of the dilator will cause a portion (1016 in FIG. 10A) of dilator 1010 to push against the free atrial wall. This in turn will transmit the longitudinal force in a lateral direction, thus forcing the distal end of dilator 1010 through the perforation. Alternatively, as shown in FIG. 14B, dilator 1030 may comprise a gentle curve which lends itself to transmitting mechanical force, such that the longitudinal force applied at a proximal end of the dilator will advance the distal end through the perforation. In such an embodiment, apparatus 102 may serve as a rail to support dilator 1030 and to ensure that dilator 1030 does not slip down the septal wall.

In order to advance the sheath and dilator, hub 114 of apparatus 102 may be fixed in place spatially, and both the proximal hub 914 of the dilator and proximal hub 804 of the sheath may be incrementally advanced forward, together, thus sliding the dilator and sheath over apparatus 102 (step 1630). The distal tip of the dilator and the distal tip of the sheath may be monitored under fluoroscopy as they are advanced over apparatus 102 and, once the tip of the dilator has traversed the perforation and has advanced into the left atrium 1112, the tip of the sheath may then be advanced over the dilator, across the perforation and into the left atrium 1112 as well (step 1632). In an alternate method of advancing the sheath and dilator into the left atrium, once distal region 106 is fully advanced through the perforation and into the left atrium 1112, and hub 114 of apparatus 102 is flush against proximal hub 914 of the dilator, hub 114 of apparatus 102, proximal hub 914 of the dilator and proximal hub 804 of the sheath may all be advanced forward together, for example under fluoroscopy. Forward momentum will cause the distal tip of the dilator to traverse the perforation, advancing into the left atrium 1112. The distal tip of the sheath will follow over the dilator, across the perforation and into the left atrium 1112. Alternatively, apparatus 102, the dilator and the sheath may each be advanced independently through the perforation. For example, the sheath may be advanced prior to the dilator.

Figure 15:
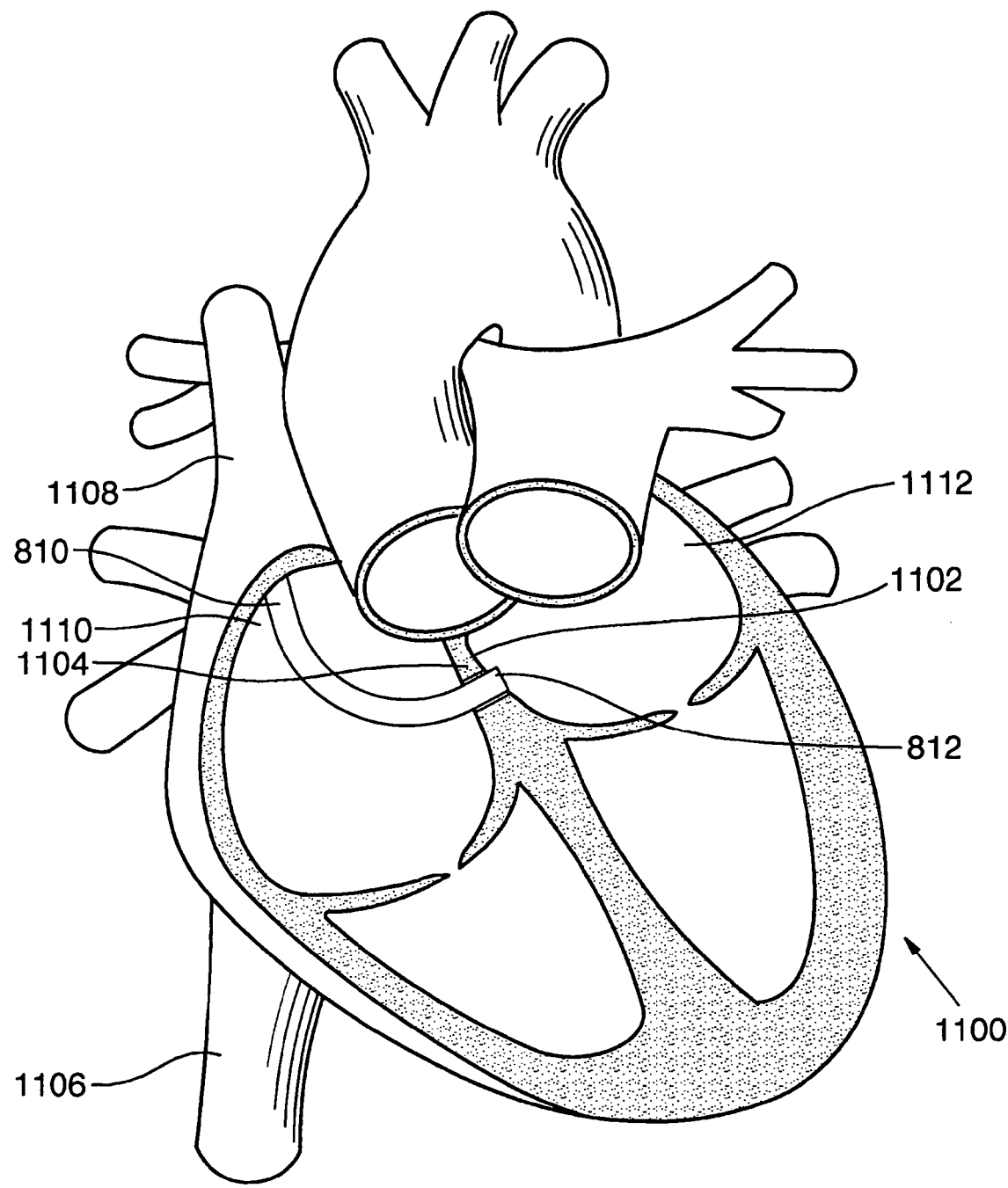
FIG. 15 illustrates a position of one embodiment of a guiding sheath of the present invention within a patient's heart.

At step 1634, the positions of distal region 106 of apparatus 102, the distal tip of the dilator and the distal tip of the sheath may be confirmed, for example, under fluoroscopy, to be in the left atrium 1112. If not in the desired location (step 1636), step 1630 may be repeated. If the positions are confirmed (step 1636), apparatus 102 and the dilator may now be respectively withdrawn outside the body, for example under fluoroscopic guidance (step 1638). While maintaining the position of the distal tip of the dilator and the distal tip of the sheath in the left atrium 1112, apparatus 102 may be withdrawn. The dilator may then be withdrawn outside the body under fluoroscopic guidance, while maintaining the position of the distal tip of the sheath in the left atrium 1112. In some embodiments (see, for example, FIG. 15), the sheath may assume its original shape once the dilator is withdrawn. In other words, while the dilator is located within the sheath lumen, the sheath may conform to the shape of the dilator. However, once the dilator is removed, the sheath may revert to its original shape, i.e. the shape it had prior to receiving the dilator within the sheath. Optionally, a contrast agent may now be injected through the sheath into the left atrium 1112, blood may be aspirated through the sheath from the left atrium 1112, or other devices (for example treatment devices or diagnostic devices) or treatment compositions may be introduced into the left atrium 1112 through the perforation (for example, through the sheath).

As has been mentioned above, it may be advantageous, particularly in embodiments wherein the heart is approached via the SVC, to employ one or more dilators of various configurations throughout the procedure. For example, a dilator having a first shape may be used to facilitate positioning of apparatus 102 adjacent the fossa ovalis or other material to be perforated. Subsequently, a dilator having a second shape may be used to facilitate advancement of the dilator across the perforation. These two dilator shapes may be achieved in a number of ways. For example, two separate dilators may be used. One embodiment may comprise two dilators which may be exchanged during the course of the procedure. In other words, one dilator may be used to position the apparatus for perforation and, after perforation has been completed, the dilator may be exchanged for a second dilator configured to facilitate advancement of the dilator across the perforation. Alternatively, another embodiment may comprise a first, more flexible dilator configured to facilitate advancement of the dilator through the perforation. A second, stiffer dilator may be located within a lumen defined by the more flexible dilator. The stiffer dilator may be configured to facilitate positioning of the apparatus for perforation. Thus, in use, the stiffer dilator may be inserted within the more flexible dilator in order to position the apparatus for perforation. Once perforation has been completed, the stiffer dilator may be retracted, thus allowing the more flexible dilator to assume its natural shape, configured to allow for advancement of the dilator through the perforation. In a further embodiment, the dilator may be configured such that a user can modify the shape of the dilator during the course of the procedure. In other embodiments, the dilator may have a single configuration throughout the procedure, as illustrated, for example, in FIGS. 13A and 14A.

The present invention in various embodiments thus provides a device and method that is capable of creating a perforation while determining a position of the device in response to action potentials or measured voltage at a location in the heart as well as determining a position of the device in response to pressure at a location in the body. In some embodiments, the present invention decreases the risk of inadvertent and unwanted cardiac injury associated with creating the perforation. One means for decreasing the risk of unwanted injury comprises a curve at the distal end of the device. In further embodiments, the present invention also provides a method for staining the area to be perforated in order to make it easier to locate during the perforation. In addition, embodiments of the present invention provide a method for delivering a dilator and sheath over the device after the perforation. Various embodiments of dilators and sheaths are described in the specification. The perforation may be created by the application of energy produced by a generator and delivered to an active tip on the device. The energy may be selected from the group consisting of electrical energy (various frequencies), radiant energy (e.g. laser) and thermal energy, amongst others. A means for determining the position of the device may comprise an ECG measuring device for monitoring action potentials or measured voltage through an active electrode in a unipolar or bipolar manner and displaying the ECG tracings on an ECG recorder. In this embodiment there is at least one active electrode at the functional tip region for monitoring action potentials which are captured and displayed as ECG tracings on an ECG recorder. A means for determining the position of the device may also comprise a pressure transmitting lumen that may be releasably coupled to an external pressure transducer. In this embodiment, there is at least one opening near the distal region of the device for blood or other fluid to enter and fill the lumen and exert a measurable pressure on a coupled external transducer. The lumen and opening may also be useful for injecting radiopaque contrast or other agents through the device. In an alternate embodiment, the means for determining the position of the device in response to pressure comprises a transducer located on the device proximal to the functional tip.

The device of the invention may be useful as a substitute for a traditional trans-septal needle to create a trans-septal perforation. Some embodiments of the device of the present invention may have a soft and curved distal region with a functional tip that uses RF energy to create a perforation across a septum, making the procedure more easily controlled and less operator dependent than a trans-septal needle procedure. The soft distal region of the device may reduce incidents of vascular trauma as the device is advanced through the vasculature. The application of RF energy may be controlled via an electric generator, eliminating the need for the operator to subjectively manage the amount of force necessary to cross the septum with a traditional needle. Thus, the present invention may reduce the danger of applying too much mechanical force and injuring the posterior wall of the heart.

The present invention also provides a method for the creation of a perforation in, for example, an atrial septum. ECG as well as pressure monitoring may be advantageous in this procedure, as there is the possibility of inadvertently perforating the aorta due to its proximity to the atrial septum. Electrical action potential or voltage measurements displayed as ECG tracings allow the operator to position the device accurately at the fossa ovalis on the septum as well as confirm that the distal end of the device has entered the left atrium, and not the aorta or another undesirable location in the heart. As well, pressure measurements allow the operator to confirm that the distal end of the device has entered the left atrium, and not the aorta, or another undesirable location in the heart. Staining the atrial septum may also be advantageous in this procedure, as it easily identifies the region of the atrial septum (fossa ovalis) to be perforated. The device may also be visible using standard imaging techniques; however the ability to monitor both ECG and pressure provides the operator with a level of safety and confidence that would not exist using only these techniques. It should be noted, however, that a method of the present invention may be practiced without any or all of pressure monitoring, ECG monitoring and staining and is thus intended to comprise, in a basic form, a method of creating a perforation in a tissue utilizing any intravascular approach.

In some embodiments of the present invention, the heart is approached via the inferior vena cava (IVC) (an 'inferior' approach). In such embodiments, the device may be introduced into the patient's vasculature via the femoral vein. In alternate embodiments, the heart may be approached via the superior vena cava (SVC) (a 'superior' approach). Such embodiments may be useful in instances where introduction via the IVC is contra-indicated, as has been discussed. In such embodiments, access to the patient's vasculature may be achieved through one or more of a brachial vein, an axillary vein, a subclavian veinn and a jugular vein.

In order to create the perforation, it may be desirable to position the device at a specific orientation relative to the material to be perforated. For example, the device may be oriented at an angle of between about 80 to about 100 degrees relative to the fossa ovalis. Achieving such an orientation using a superior approach may require the use of dilators and/or sheaths having appropriate shapes, as has been described herein above.

The present invention also provides a method for delivering the dilator and sheath over the device into the left atrium once a successful perforation has been created. Once again, in order to successfully advance the dilator and/or sheath through the perforation when using a superior approach, it may be advantageous to employ devices with appropriate shapes and configurations, as has been described.

One of the motivations for creating a trans-septal perforation is to gain access to the left side of the heart for delivery of catheters or devices to treat left-sided heart arrhythmias or defects. An application of a method aspect of the present invention may involve the implantation of a device, such as an implantable pressure monitor or other sensor into the left atrium of a patient's heart. Using an embodiment of a method aspect of the present invention, a perforation may be created between the right and left atria of a patient's heart utilizing a superior intravascular approach, for example through a subclavian vein. Following the creation of the perforation, an implantable device may be inserted through to the left atrium and implanted at a desired location. In one embodiment, the implantable device may be initially mounted on one of an electrosurgical device, a dilator, a sheath or a guidewire, thus obviating the need for an additional device to insert the implantable device. In additional embodiments, a pressure sensor or other device may be inserted into the left atrium after the creation of a perforation in order to monitor pressure or some other physiological parameter without being permanently implanted. In other words, the device may be used to monitor some parameter and may then be removed, in the same procedure, without being permanently implanted into the patient. All of these applications are intended to be exemplary only and are not intended to limit the scope of the present invention in any way.

While the surgical device thus described is capable of perforating living tissue, it will be understood by persons of ordinary skill in the art that an appropriate device in accordance with the invention will be capable of perforating or removing material such as plaque or thrombotic occlusions from diseased vessels as well. Furthermore, any of the hubs referred to throughout this specification (e.g. hub 114, hub 804 and hub 914) may be removable in order to facilitate exchange or removal of any devices or components during the course of a procedure.

Persons of ordinary skill in the art will appreciate that one or more features of the device and method aspects of the present invention are optional. For example, a device may be made within the scope of the invention without a curve portion of the distal region. Further, a pressure sensing mechanism for positioning the device is optional and, in other instances, the ECG monitoring feature is optional.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of surgical perforation via the delivery of electrical, radiant or thermal energy comprising the steps of:
    (i) introducing an apparatus comprising an energy delivery device into a patient's heart via said patient's superior vena cava, said apparatus further comprising at least one pressure sensing mechanism selected from the group consisting of a pressure-transmitting lumen and a pressure transducer;
    (ii) positioning said energy delivery device at a first location adjacent material to be perforated;
    (iii) perforating said material by delivering energy via said energy delivery device;
    (iv) advancing said energy delivery device to a second location through the perforation, said second location being a left atrium of said patient's heart; and
    (v) measuring pressure at said second location;
    wherein said energy is selected from the group consisting of electrical energy, radiant energy and thermal energy.

2. The method as claimed in claim 1, wherein step (ii) comprises positioning said energy delivery device at an angle of about 80 degrees to about 100 degrees relative to said material to be perforated.

3. The method as claimed in claim 2, wherein step (ii) comprises positioning said energy delivery device substantially perpendicularly relative to said material to be perforated.

4. The method as claimed in claim 1 wherein said apparatus further comprises a distal region capable of adopting a curved shape and wherein step (iv) further comprises directing a distal tip of said apparatus in a desired direction.

5. The method as claimed in claim 4, wherein said distal tip is directed away from cardiac structures in order to decrease risk of unwanted injury.

6. The method as claimed in claim 4 wherein said apparatus further comprises an orientation indicator for determining a direction of said distal tip and wherein said method comprises monitoring said orientation indicator.

7. The method as claimed in claim 1 wherein step (ii) comprises staining at least a portion of said first location with a radiopaque dye.

8. The method as claimed in claim 1 wherein the step of introducing an apparatus comprises the steps of:
    (a) introducing said apparatus into said patient's vasculature; and
    (b) advancing said apparatus through said patient's vasculature into said patient's heart.

9. The method as claimed in claim 8 wherein step (a) comprises inserting said apparatus into a vein selected from the group consisting of a jugular vein, a subclavian vein, a brachial vein and an axillary vein.

10. The method as claimed in claim 1, wherein step (i) further comprises inserting a dilator and a sheath into said patient's heart.

11. The method as claimed in claim 10, wherein step (ii) comprises positioning said dilator such that a distal end of said dilator is oriented at an angle of about 80 degrees to about 100 degrees relative to said material to be perforated.

12. The method as claimed in claim 11, wherein step (ii) comprises positioning said dilator such that a distal end of said dilator is oriented substantially perpendicularly relative to said material to be perforated.

13. The method as claimed in claim 10, further comprising advancing said energy delivery device, said dilator and said sheath to a second location through the perforation.

14. The method as claimed in claim 13, wherein said dilator is shaped such that a distal end of said dilator will be advanced through said perforation upon an application of a longitudinal force onto a proximal end of said dilator.

15. The method as claimed in claim 1 wherein said material to be perforated is tissue of an atrial septum of said patient's heart.

16. The method as claimed in claim 15, wherein said material comprises a fossa ovalis of said patient's heart.

17. The method as claimed in claim 1, further comprising a step of delivering one or more of a treatment device, a diagnostic device and a treatment composition through said perforation.

18. A method of surgical perforation via the delivery of electrical, radiant or thermal energy comprising the steps of:
    (i) introducing an apparatus comprising an energy delivery device into a patient's heart via said patient's superior vena cava;
    (ii) positioning said energy delivery device at a first location adjacent material to be perforated;
    (iii) perforating said material by delivering energy via said energy delivery device; and
    (iv) monitoring ECG in said patient's heart using said apparatus;
    wherein said energy is selected from the group consisting of electrical energy, radiant energy and thermal energy.

19. The method as claimed in claim 18, wherein step (ii) comprises dragging said energy delivery device about a surface of said patient's heart while monitoring ECG in order to determine said first location.

20. The method as claimed in claim 19, wherein said ECG at said first location comprises a damped signal in comparison with ECG monitored otherwise on said surface of said patient's heart.

21. A method of surgical perforation comprising the steps of:
   (i) introducing an apparatus into a patient's heart via said patient's superior vena cava, said apparatus comprising an energy delivery device and a means for determining the position of said energy delivery device, said means for determining position comprising at least one pressure sensing mechanism selected from the group consisting of a pressure transmitting lumen and a pressure transducer; and
   (ii) positioning said energy delivery device adjacent material to be perforated in response to the means for determining position.

22. The method as claimed in claim 21 further comprising the step of:
   (iii) perforating said material by delivering energy via said energy delivery device.

23. The method as claimed in claim 22, wherein said energy comprises radiant energy.

24. The method as claimed in claim 22, wherein said energy comprises electrical energy.

25. The method as claimed in claim 22, wherein said energy comprises thermal energy.

26. A method of surgical perforation comprising the steps of:
   (i) introducing an apparatus into a patient's heart via said patient's superior vena cava, said apparatus comprising an energy delivery device and a means for determining the position of said energy delivery device, said means for determining position comprising an ECG measuring device; and
   (ii) positioning said energy delivery device adjacent material to be perforated in response to the means for determining position.

27. The method as claimed in claim 26 further comprising the step of:
   (iii) perforating said material by delivering energy via said energy delivery device.

28. The method as claimed in claim 27, wherein said energy comprises radiant energy.

29. The method as claimed in claim 27, wherein said energy comprises electrical energy.

30. The method as claimed in claim 27, wherein said energy comprises thermal energy.

* * * * *